United States Patent [19]

Aotsuka et al.

[11] Patent Number: 5,700,819
[45] Date of Patent: Dec. 23, 1997

[54] 2-SUBSTITUTED BENZOTHIAZOLE DERIVATIVES AND PROPHYLACTIC AND THERAPEUTIC AGENTS FOR THE TREATMENT OF DIABETIC COMPLICATIONS

[75] Inventors: Tomoji Aotsuka; Naoki Abe; Naoki Ashizawa, all of Hamura, Japan

[73] Assignee: Grelan Pharmaceutical Co., Ltd., Tokyo, Japan

[21] Appl. No.: 562,061

[22] Filed: Nov. 22, 1995

[30] Foreign Application Priority Data

Nov. 29, 1994 [JP] Japan ................. 6-317809

[51] Int. Cl.$^6$ ................. A61K 31/425; C07D 277/64
[52] U.S. Cl. ................. 514/367; 548/170; 548/180
[58] Field of Search ................. 548/170, 180; 514/367

[56] References Cited

U.S. PATENT DOCUMENTS

| | | | |
|---|---|---|---|
| 4,325,959 | 4/1982 | Matthews | 424/270 |
| 5,152,929 | 10/1992 | Bentley et al. | 252/391 |
| 5,347,008 | 9/1994 | Bentley et al. | 548/170 |

FOREIGN PATENT DOCUMENTS

| | | |
|---|---|---|
| 0 222 576 | 5/1987 | European Pat. Off. |
| 0 295 051 | 12/1988 | European Pat. Off. |
| 0 322 153 | 6/1989 | European Pat. Off. |
| 0 492 667 A1 | 7/1992 | European Pat. Off. |
| 94/15934 | 7/1994 | WIPO |
| 94/22845 | 10/1994 | WIPO |
| 94/22875 | 10/1994 | WIPO |

OTHER PUBLICATIONS

Database WPI, Week 9429, Derwent Publications Ltd. London, GB; AN 94-238744 & JP-A-06 172 353 (Green Cross Corp.), 21 Jun. 1994 *abstract*.

Chemical Abstracts, vol. 123, No. 112057p, 1995.
Chemical Abstracts, vol. 122, No. 214086u, 1995.
Chemical Abstracts, vol. 122, No. 239686c, 1995.
Chemical Abstracts, vol. 121, No. 280632z, 1994.
Chemical Abstracts, vol. 121, No. 280655j, 1994.
Chemical Abstracts, vol. 117, No. 151006s, 1992.
Chemical Abstracts, vol. 103, No. 160493m, 1985.
Aotsuka et al., "Novel and Potent Aldose Reductase Inhibitors: 4-Benzyl-and 4-(Benzothiazol-2-ylmethyl)-3,4-dihydro-3-oxo-2H-1,4-benzothiazine-2-acetic Acid Derivatives", Chem. Pharm. Bull. 42(6), pp. 1264-1271, 1994.

*Primary Examiner*—Johann Richter
*Assistant Examiner*—Laura Cross Lutz
*Attorney, Agent, or Firm*—Wenderoth, Lind & Ponack

[57] ABSTRACT

Unique benzothiazole derivatives which exert superior aldose redactase inhibiting actions are unexpectedly and advantageously useful in the prophylactic and therapeutic treatment of diabetic complications. A benzothiazole derivative compound of the formula (1):

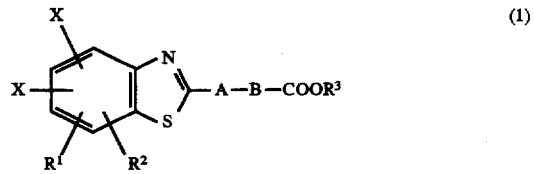

(1)

wherein X is halogen, $R^1$ and $R^2$, which are the same or different, are each independently hydrogen or halogen, A is a methylene group or a sulfur atom, and $-B-COOR^3$ is a group as defined in the specification; or a pharmaceutically acceptable salt and a pharmaceutical composition comprising the same which is a useful prophylactic or therapeutic agent for the treatment of diabetic complications.

14 Claims, No Drawings

2-SUBSTITUTED BENZOTHIAZOLE DERIVATIVES AND PROPHYLACTIC AND THERAPEUTIC AGENTS FOR THE TREATMENT OF DIABETIC COMPLICATIONS

BACKGROUND OF THE INVENTION

The present invention relates to novel 2-substituted benzothiazole derivatives having potent pharmacological actions and intermediates for the preparation thereof. More particularly, the present invention relates to compounds having potent aldose reductase-inhibitory activity, which are useful as prophylactic and therapeutic agents for treating diseases such as diabetic complications. The present invention also relates to pharmaceutical compositions comprising an effective amount of said 2-substituted benzothiazole derivative and a pharmaceutically acceptable carrier useful in treating diabetes-related diseases.

DESCRIPTION OF RELATED ART

The incidence of diabetes has been increasing, and insulin and a variety of euglycemic agents have been used as medicaments for remedying diabetes. However, their efficacy against diabetic complications, which are becoming a serious problem with higher incidence of diabetes, is limited. Therefore, the development of new therapeutic agents for diabetic complications is desired in view of novel concepts.

In diabetic hyperglycemia, because of elevated glucose level in insulin-independent tissues such as peripheral nerves, retina, lens, cornea, blood vessels and glomeruli, glucose metabolism through the polyol pathway in these tissues is activated, and polyols such as sorbitol are accumulated. The diabetic hyperglycemia causes diabetic complications due to the accumulation of polyols. Accordingly, techniques for preventing and treating diabetic complications by inhibiting aldose reductase, a glucose metabolizing enzyme, are studied.

Among the compounds synthesized with the aim of inhibitor of aldose reductase, some benzothiazole derivatives are disclosed in prior art documents, for example: Japanese Unexamined Patent Publications No. 3173/1989, No. 211585/1989, No. 5481/1991, No. 234321/1992, No. 92961/1993 (Chemical Abstracts (CA), Vol. 117, 151006s, 1992; EP No. 492,667), No. 172353/1994 (CA, Vol. 121, 280655j, 1994), No. 199851/1994 (CA, Vol. 121, 280632z, 1994; WO 94 15,934), No. 279423/1994 (CA, Vol. 122, 239686c, 1995; WO 94 22,845) and No. 279453/1994 (CA, Vol. 122, 214086u, 1995; WO 94 22,875). However, these compounds are not satisfactory medicaments, so the development of drugs with higher aldose reductase inhibiting activity, for the treatment of diabetic complications, is still desired.

SUMMARY OF THE INVENTION

The present invention provides novel 2-substituted benzothiazole derivatives having potent aldose reductase-inhibiting activity, which are of practical value in clinical use as prophylactic and therapeutic agents.

The present invention relates to 2-substituted benzothiazole derivatives having the formula (1):

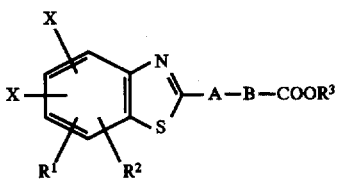

(1)

wherein X is halogen, $R^1$ and $R^2$, which are the same or different, are each independently hydrogen or halogen, A is a methylene group or a sulfur atom, and —B—$COOR^3$ is a group represented by the following formula (2):

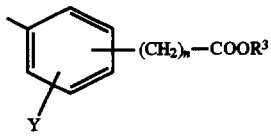

(2)

wherein $R^3$ is hydrogen or C1 to C3 lower alkyl, Y is hydrogen, halogen, C1 to C3 lower alkyl, carboxyl or dilower alkylamino and n is an integer of 1 to 3; a group represented by the following formula (3):

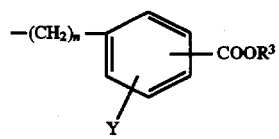

(3)

wherein $R^3$ is hydrogen or C1 to C3 lower alkyl, Y is hydrogen, halogen, C1 to C3 lower alkyl, carboxyl or dilower alkylamino and n is an integer of 1 to 3; a group represented by the following formula (4):

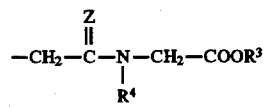

(4)

wherein Z is oxygen or sulfur, $R^3$ is hydrogen or C1 to C3 lower alkyl, $R^4$ is C1 to C3 lower alkyl, optionally substituted phenyl, optionally substituted benzyl or optionally substituted phenethyl; or a group represented by the following formula (5):

$$-(CH_2)_m-COOR^3 \qquad (5)$$

wherein $R^3$ is hydrogen or C1 to C3 lower alkyl, and m is an integer of 2 to 5, provided that, when —B—$COOR^3$ is the formula (5), A is methylene, or a pharmaceutically acceptable salt thereof.

Another aspect of the present invention relates to pharmaceutical compositions comprising an effective amount of the 2-substituted benzothiazole derivative having the formula (1) or a pharmaceutically acceptable salt thereof in admixture with a pharmaceutically acceptable carrier useful in inhibiting aldose reductase.

Still another aspect of the present invention relates to processes for producing such compounds and compositions.

Yet another aspect of the present invention relates to a method for treating said diseases of mammalia, which comprises administering an effective amount of the 2-substituted benzothiazole derivative having the formula (1) or the pharmaceutical composition thereof to said mammalia.

DETAILED DESCRIPTION OF THE PREFERRED EMBODIMENT

The present invention provides the 2-substituted benzothiazole derivatives (1) and the pharmaceutically acceptable salts thereof, which possess strong aldose reductase-inhibiting activity and are of value in the prophylactic or therapeutic treatment of diabetic complications; a pharmaceutical composition comprising an effective amount of the 2-substituted benzothiazole derivative having the formula (1) or a pharmaceutically acceptable salt thereof in admixture with a pharmaceutically acceptable carrier useful as an inhibitor of aldose reductase; and processes for producing such compounds and compositions. The present invention further provides a method for treating said diseases of mammalia, which comprises administering an effective amount of the 2-substituted benzothiazole derivative having the formula (1) or the pharmaceutical composition thereof to said mammalia.

With regard to the foregoing formula (1), X is halogen including, for example, fluorine and chlorine. Among them, fluorine is preferable.

$R^1$ and $R^2$, which are the same or different, are each independently hydrogen or halogen. Halogen for $R^1$ and $R^2$ includes, for example, fluorine and chlorine. Among them, fluorine is preferable.

With regard to the foregoing formulas (2) and (3), $R^3$ is hydrogen or C1 to C3 lower alkyl. C1 to C3 lower alkyl groups for $R^3$ include, for example, methyl, ethyl, n-propyl and isopropyl. Y is hydrogen, halogen, C1 to C3 lower alkyl, carboxyl or dilower alkylamino. Halogen for Y includes, for example, fluorine, chlorine, bromine and iodine. C1 to C3 lower alkyl groups for Y include, for example, methyl, ethyl, n-propyl and isopropyl. Dilower alkylamino groups for Y include, for example, dimethylamino, diethylamino, di(n-propyl)amino and diisopropylamino.

With regard to the foregoing formula (4), $R^4$ is C1 to C3 lower alkyl, optionally substituted phenyl, optionally substituted benzyl or optionally substituted phenethyl. C1 to C3 lower alkyl groups for $R^4$ include, for example, methyl, ethyl, n-propyl and isopropyl. Optionally substituted phenyl groups, optionally substituted benzyl groups and optionally substituted phenethyl groups for $R^4$ include, for example, phenyl, benzyl and phenethyl groups which may be substituted with, for example, halogen (e.g. F, Cl, Br, etc.), lower (C1–C3) alkyl (e.g. methyl, ethyl, n-propyl, isopropyl, etc.), or the like at various positions of the benzene ring. Among the above-mentioned phenyl, benzyl and phenethyl groups, preferred examples are phenyl, benzyl and phenethyl; phenyl, benzyl and phenethyl substituted with halogen (e.g., F, Cl, Br, etc.); and phenyl, benzyl and phenethyl substituted with lower (C1–C3) alkyl (e.g., methyl, ethyl, n-propyl, isopropyl).

An important group of compounds according to the present invention are the compounds of the formula (6):

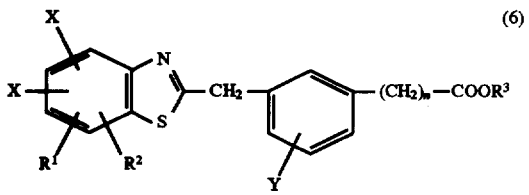

wherein X is halogen, $R^1$ and $R^2$, which are the same or different, are each independently hydrogen or halogen, $R^3$ is hydrogen or C1 to C3 lower alkyl, Y is hydrogen, halogen, C1 to C3 lower alkyl, carboxyl or dilower alkylamino and n is an integer of 1 to 3 or the pharmaceutically acceptable salts thereof.

The compounds of the present invention include benzothiazole derivatives of the formula (1) wherein —B—COOR$^3$ is a group represented by the aforementioned formula (2). Preferred benzothiazole derivatives include compounds of the formula (6):

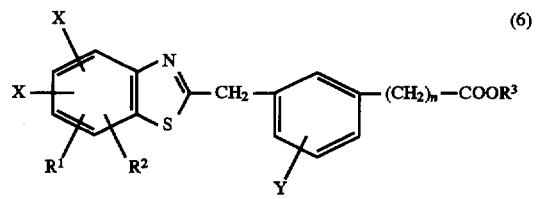

wherein X, $R^1$, $R^2$, $R^3$, Y and n are of the same meaning as defined above.

Preferred examples of said compounds according to the present invention include:

(1) 3-[(4,5-difluorobenzothiazol-2-yl)methyl]phenylacetic acid (2) 3-[(4,5-dichlorobenzothiazol-2-yl)methyl]phenylacetic acid (3) 3-[(4,5,7-trifluorobenzothiazol-2-yl)methyl]phenylacetic acid (4) 3-[(4,5,7-trifluorobenzothiazol-2-yl)methyl]phenylpropionic acid (5) a methyl, ethyl, n-propyl and i-propyl ester each of the above-mentioned carboxylic acids (1) to (4).

The compounds of the present invention include benzothiazole derivatives of the formula (1) wherein —B—COOR$^3$ is a group represented by the aforementioned formula (3). Preferred benzothiazole derivatives include compounds of the formula (7):

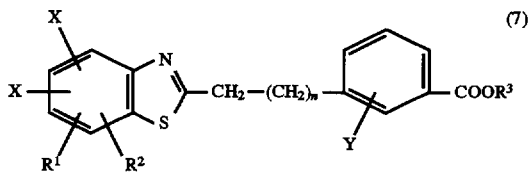

wherein X, $R^1$, $R^2$, $R^3$, Y and n are of the same meaning as defined above.

Preferred examples of said compounds according to the present invention include:

(1) 3-[2-(4,5-difluorobenzothiazol-2-yl)ethyl]benzoic acid (2) 3-[2-(4,5-dichlorobenzothiazol-2-yl)ethyl]benzoic acid (3) 3-[2-(4,5,7-trifluorobenzothiazol-2-yl)ethyl]benzoic acid (4) 3-[3-(4,5,7-trifluorobenzothiazol-2-yl)propyl]benzoic acid (5) a methyl, ethyl, n-propyl and i-propyl ester each of the above-mentioned carboxylic acids (1) to (4).

The compounds of the present invention include benzothiazole derivatives of the formula (1) wherein —B—COOR$^3$ is a group represented by the aforementioned formula (4). Preferred benzothiazole derivatives include compounds of the formula (8):

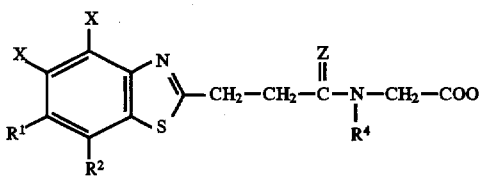

wherein X, Z, R¹, R², R³ and R⁴ are of the same meaning as defined above, and compounds of the formula (9):

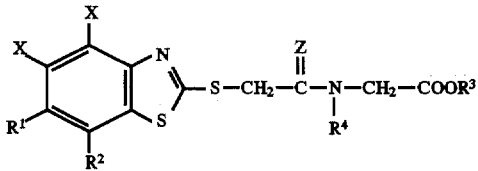

wherein X, Z, R¹, R², R³ and R⁴ are of the same meaning as defined above.

Preferred examples of said compounds according to the present invention include:

(1) N-[3-(4,5-difluorobenzothiazol-2-yl)propionyl]-N-methylglycine
(2) N-[3-(4,5-dichlorobenzothiazol-2-yl)propionyl]-N-methylglycine
(3) N-[3-(4,5,7-trifluorobenzothiazol-2-yl)propionyl]-N-methylglycine
(4) N-[3-(4,5,7-trifluorobenzothiazol-2-yl)propionyl]-N-phenylglycine
(5) N-benzyl-N-[3-(4,5,7-trifluorobenzothiazol-2-yl)propionyl]-glycine
(6) N-[3-(4,5,7-trifluorobenzothiazol-2-yl)propionyl]-N-phenethylglycine
(7) N-[3-(4,5-difluorobenzothiazol-2-yl)-1-thioxopropyl]-N-methylglycine
(8) N-[3-(4,5-dichlorobenzothiazol-2-yl)-1-thioxopropyl]-N-methylglycine
(9) N-[3-(4,5,7-trifluorobenzothiazol-2-yl)-1-thioxopropyl]-N-methylglycine
(10) N-[3-(4,5,7-trifluorobenzothiazol-2-yl)-1-thioxopropyl]-N-phenylglycine
(11) N-benzyl-N-[3-(4,5,7-trifluorobenzothiazol-2-yl)-1-thioxopropyl]glycine
(12) N-[3-(4,5,7-trifluorobenzothiazol-2-yl)-1-thioxopropyl]-N-phenethylglycine
(13) N-[2-(4,5,7-trifluorobenzothiazol-2-ylthio)acetyl]-N-phenylglycine
(14) a methyl, ethyl, n-propyl and i-propyl ester each of the above-mentioned carboxylic acids (1) to (13).

The compounds of the present invention include benzothiazole derivatives of the formula (1) wherein —B—COOR³ is a group represented by the aforementioned formula (5). Preferred benzothiazole derivatives include compounds of the formula (10):

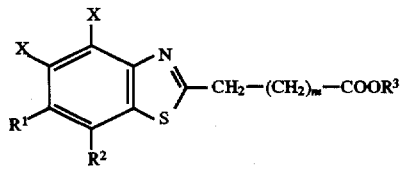

wherein X, R¹, R², R³ and m are of the same meaning as defined above, and compounds of the formula (11):

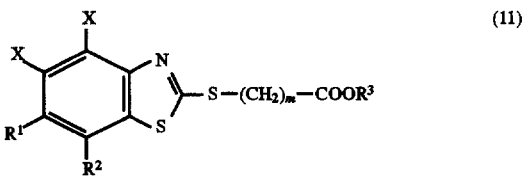

wherein X, R¹, R², R³ and m are of the same meaning as defined above.

Preferred examples of said compounds according to the present invention include:

(1) 4-(4,5,7-trifluorobenzothiazol-2-yl)butanoic acid
(2) 5-(4,5,7-trifluorobenzothiazol-2-yl)pentanoic acid
(3) 6-(4,5-difluorobenzothiazol-2-yl)hexanoic acid
(4) 6-(4,5,7-trifluorobenzothiazol-2-yl)hexanoic acid
(5) 7-(4,5,7-trifluorobenzothiazol-2-yl)heptanoic acid
(6) 5-(4,5-difluorobenzothiazol-2-ylthio)pentanoic acid
(7) 5-(4,5,7-trifluorobenzothiazol-2-ylthio)pentanoic acid
(8) a methyl, ethyl, n-propyl and i-propyl ester each of the above-mentioned carboxylic acids (1) to (7).

Preferred examples of the concrete compounds according to the invention are:

(1) 2-[(4,5,7-trifluorobenzothiazol-2-yl)methyl]phenylacetic acid
(2) 4-[(4,5,7-trifluorobenzothiazol-2-yl)methyl]phenylacetic acid
(3) 3-[(5,7-difluorobenzothiazol-2-yl)methyl]phenylacetic acid
(4) 3-[(6,7-difluorobenzothiazol-2-yl)methyl]phenylacetic acid
(5) 3-[(4,5-difluorobenzothiazol-2-yl)methyl]-5-methylphenylacetic acid
(6) 3-[(4,5-difluorobenzothiazol-2-yl)methyl]-5-ethylphenylacetic acid
(7) 3-[(4,5-difluorobenzothiazol-2-yl)methyl]-5-fluorophenylacetic acid
(8) 3-[(4,5-difluorobenzothiazol-2-yl)methyl]-5-chlorophenylacetic acid
(9) 3-[(4,5-difluorobenzothiazol-2-yl)methyl]-5-bromophenylacetic acid
(10) 3-[(4,5-difluorobenzothiazol-2-yl)methyl]-5-iodophenylacetic acid
(11) 3-[(4,5-difluorobenzothiazol-2-yl)methyl]-5-carboxylphenylacetic acid
(12) 3-[(4,5-difluorobenzothiazol-2-yl)methyl]-5-dimethylaminophenylacetic acid
(13) 3-[(4,5,7-trifluorobenzothiazol-2-yl)methyl]-2-chlorophenylacetic acid
(14) 3-[(4,5,7-trifluorobenzothiazol-2-yl)methyl]-5-methylphenylacetic acid
(15) 3-[(4,5,7-trifluorobenzothiazol-2-yl)methyl]-5-fluorophenylacetic acid
(16) 3-[(4,5,7-trifluorobenzothiazol-2-yl)methyl]-5-chlorophenylacetic acid
(17) 3-[(4,5,7-trifluorobenzothiazol-2-yl)methyl]-5-bromophenylacetic acid
(18) 3-[(4,5,7-trifluorobenzothiazol-2-yl)methyl]-5-iodophenylacetic acid
(19) 3-[(4,5,7-trifluorobenzothiazol-2-yl)methyl]-5-carboxylphenylacetic acid
(20) 3-[(4,5,7-trifluorobenzothiazol-2-yl)methyl]-5-dimethylaminophenylacetic acid

(21) a methyl, ethyl, n-propyl and i-propyl ester each of the above-mentioned carboxylic acids (1) to (20).

The compound (1) may be in the form of salts (including addition salts) derived from pharmaceutically or physiologically acceptable acids or bases. Such salts include medically or pharmaceutically acceptable non-toxic or low toxic basic salts or acid salts. These salts include but are not limited to the following: basic salts with ammonium, an alkali metal or alkaline earth metal, such as lithium, sodium, potassium, calcium and magnesium or with an organic base (e.g., trialkylamines such as triethylamine, dibenzylamine, ethanolamine, triethanolamine, N-methylmorpholine and pyridine, etc.) and acid salts with an inorganic acid such as hydrochloric acid, hydrobromic acid, hydroiodic acid, sulphuric acid, nitric acid and phosphoric acid and, depending on compounds, salts with an organic acid such as acetic acid, propionic acid, oxalic acid, succinic acid, citric acid, ascorbic acid, lactic acid, p-toluenesulfonic acid, methanesulfonic acid, fumaric acid, tartaric acid and maleic acid.

The compounds (1) of the present invention can be made by one of various routes. The nature of the substituents involved determines the preferred method of preparation. Many compounds of Formula (1) can be prepared by one of the following schemes, as illustrated below for a preferred compound.

(A) Preferred compounds of Formula (6)

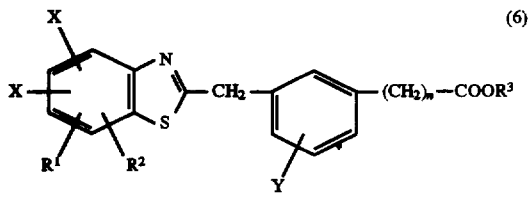

wherein X, $R^1$, $R^2$, $R^3$, Y and n are previously defined, can be prepared, for example, by the method described in Preparation Scheme 1.

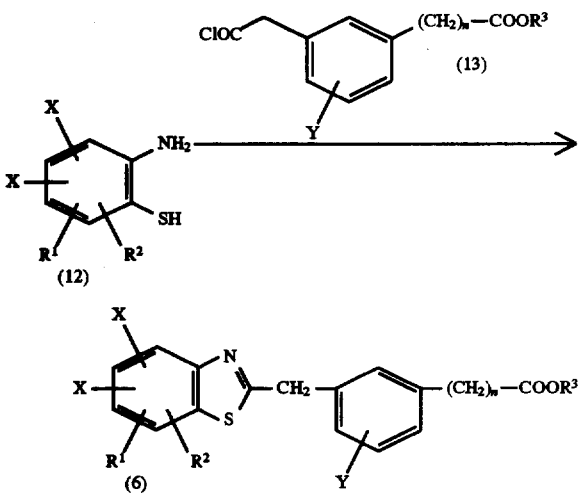

In Preparation Scheme 1, the compounds of Formula (6) can be prepared by combining an appropriate compound of Formula (12) wherein X, $R^1$ and $R^2$ are previously defined, or an acid addition salt thereof, with an appropriately substituted compound of Formula (13) wherein $R^3$, Y and n are previously defined. The reaction is carried out, if necessary, in the presence of an appropriate base, preferably under an inert gas atmosphere. In Preparation Scheme 1, the acid chloride of Formula (13) can be replaced with an appropriate reactive derivative thereof known per se such as an ester derivative thereof and an acid anhydride thereof in addition to its free carboxylic acid itself. The reaction is best carried out in the presence of or in the absence of a solvent. When the reaction is conducted in solvents, it is often convenient to use conventional solvents which are free from any adverse action on the reaction. Preferred examples of such solvents are N, N-dimethylformamide, N-methylpyrrolidone, etc. The reaction temperature range is about 20° C. to 200° C. and preferably about 60° C. to reflux.

When the compound of Formula (6) thus obtained is in the form of an ester, the ester can be converted to a corresponding carboxylic acid compound by hydrolysis in the presence of bases or acids. Preferred bases used in this hydrolysis include, for example, alkali metal hydroxides such as sodium hydroxide and potassium hydroxide, alkali metal carbonates such as sodium carbonate and potassium carbonate, etc. Preferred acids include, for example, organic acids such as formic acid, acetic acid, propionic acid, trifluoroacetic acid, benzenesulfonic acid and p-toluenesulfonic acid, inorganic acids such as hydrochloric acid, hydrobromic acid, sulphuric acid, nitric acid and phosphoric acid, and the like. The hydrolysis can be conducted in conventional solvents or mixtures thereof which are free from any adverse action on the reaction. Examples of such solvents are water, acetone, dioxane, dichloromethane, methanol, ethanol, propanol, pyridine, N, N-dimethylformamide, etc. If the base or acid used in this reaction is a form of the solution, it can be used as a solvent of the reaction. The reaction temperature range is not limited to but it can be run at temperatures within the range of cooling to heating.

The compounds of Formula (12) used in Preparation Scheme 1 may be prepared according to the known method described in Journal of Medicinal Chemistry, 34, pp.108–122, 1991, the disclosure of which is herein incorporated by reference. The compounds of Formula (13) may also be prepared according to the known method described in International Journal of Preparative Protein Research, 29, pp.331–346, 1987, the disclosure of which is herein incorporated by reference.

(B) Preferred compounds of Formula (7)

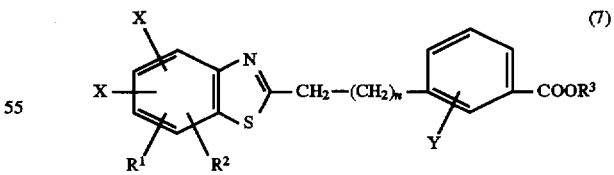

wherein X, $R^1$, $R^2$, $R^3$, Y and n are previously defined, can be prepared, for example, by the method described in Preparation Scheme 2.

Preparation Scheme 2

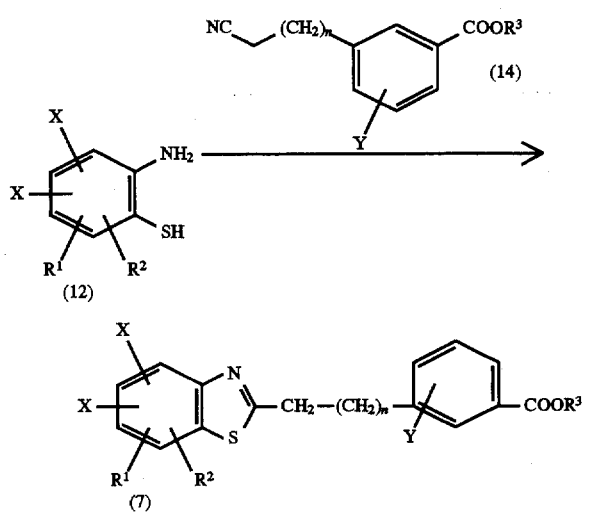

In Preparation Scheme 2, the compounds of Formula (7) can be prepared by combining an appropriate compound of Formula (12) wherein X, $R^1$ and $R^2$ are previously defined, or an acid addition salt thereof, with an appropriately substituted compound of Formula (14) wherein $R^3$, Y and n are previously defined. The reaction is carried out, preferably under an inert gas atmosphere. The reaction is best carried out in the presence of or in the absence of a solvent. When the reaction is conducted in solvents, it is often convenient to use conventional solvents which are free from any adverse action on the reaction. Preferred examples of such solvents are lower alcohols such as methanol, ethanol, propanol, and the like. The reaction temperature range is about 20° C. to about 200° C., preferably about 60° C. to the reflux temperature of solvents used. When the reaction is conducted in the absence of solvents, the acid addition salt compound of Formula (12) and the compound of Formula (14) are condensed together at about 90° C. to about 250° C. to lead to reaction. Hydrolysis of the ester product thus prepared may be conducted by methods as described for Preparation Scheme 1.

(C) Preferred compounds of Formula (8)

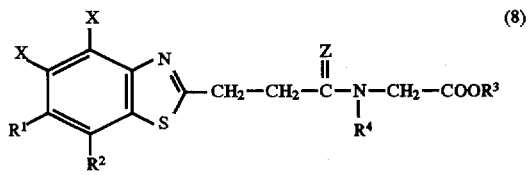

wherein X, Z, $R^1$, $R^2$, $R^3$ and $R^4$ are previously defined, can be prepared, for example, by the method described in Preparation Scheme 3.

Preparation Scheme 3

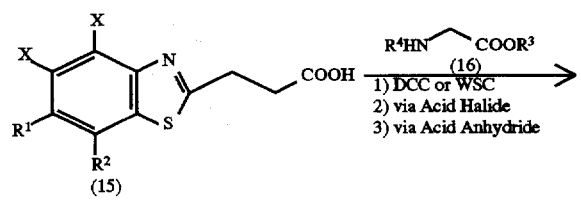

—continued
Preparation Scheme 3

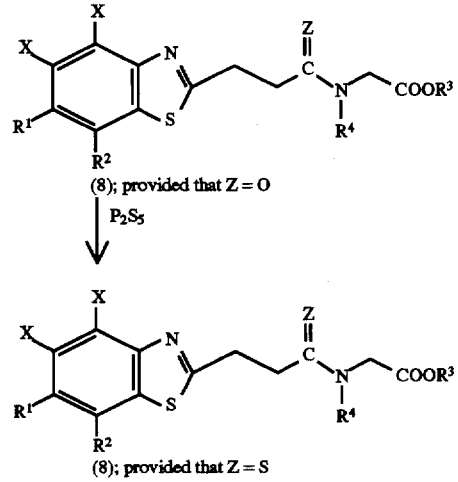

(8); provided that Z = O $$\downarrow P_2S_5$$

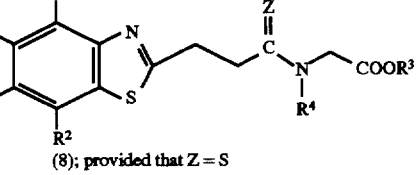

(8); provided that Z = S

In Preparation Scheme 3, the compounds of Formula (8) can be prepared by condensing an appropriate compound of Formula (15) wherein X, $R^1$ and $R^2$ are previously defined, with an appropriately substituted compound of Formula (16) wherein $R^3$ and $R^4$ are previously defined. The reaction may be carried out according to 1) techniques using dehydrating or condensing agents such as DCC (dicyclohexylcarbodiimide) or WSC (1-(3-dimethylaminopropyl)-3-ethylcarbodiimide), 2) methods via acid halides, 3) methods via mixed acid anhydrides, or the like.

The reaction 1) can be carried out using a condensing agent such as DCC or WSC in the presence of or in the absence of a tertiary amine in a solvent. Preferred examples of such solvents are methylene chloride, tetrahydrofuran, chloroform, diethyl ether, benzene, toluene, N,N-dimethylformamide, etc. Preferred tertiary amines may include pyridine, triethylamine, picoline, etc.

In the reaction 2), the carboxylic acid compound of Formula (15) is reacted with an appropriate acid halide such as thionyl chloride and oxalyl chloride, in the presence of or in the absence of the same solvent as in the aforementioned reaction 1) at −20° C. to reflux temperature and the resultant intermediate acid halide of Formula (15) is reacted with the compound of Formula (16) using the same solvent and tertiary amine as used in the aforementioned reaction 1).

In the reaction 3), the carboxylic acid compound of Formula (15) is reacted with an appropriate acid halide such as ethyl chloroformate, pivaloyl chloride, tosyl chloride and mesyl chloride, in the presence of or in the absence of the same solvent as in the aforementioned reaction 1) and in the presence of the same tertiary amine as used in the aforementioned reaction 1) and the resultant intermediate acid anhydride of Formula (15) is reacted with the compound of Formula (16) in the same solvent as in the aforementioned reaction 1).

Reaction steps are preferably run at temperatures within the range of about 20° C. to about 60° C. in an inert gas atmosphere (e.g., argon, nitrogen, etc.) under anhydrous conditions.

The compound of Formula (8) wherein Z is O, obtained according to the aforementioned steps, is reacted with a sulfurating agent such as phosphorus pentasulfide in a solvent to produce the compound of Formula 8) wherein Z is S. The reaction is usually carried out in conventional solvents which are free from any adverse action on the reaction. Preferred examples of such solvents are benzene, toluene, xylene, hexane, etc. The reaction temperature range is about −20° C. to reflux.

The ester product of Formula (8) thus prepared may be hydrolyzed in the same manner as the process for the compound of Formula (6), depending on necessity.

(D) Preferred compounds of Formula (9)

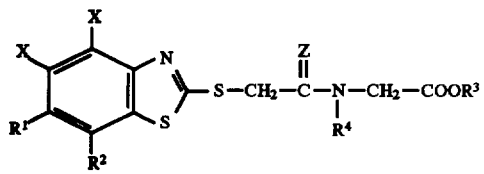

wherein X, Z, $R^1$, $R^2$, $R^3$ and $R^4$ are previously defined, can be prepared, for example, by the method described in Preparation Scheme 4.

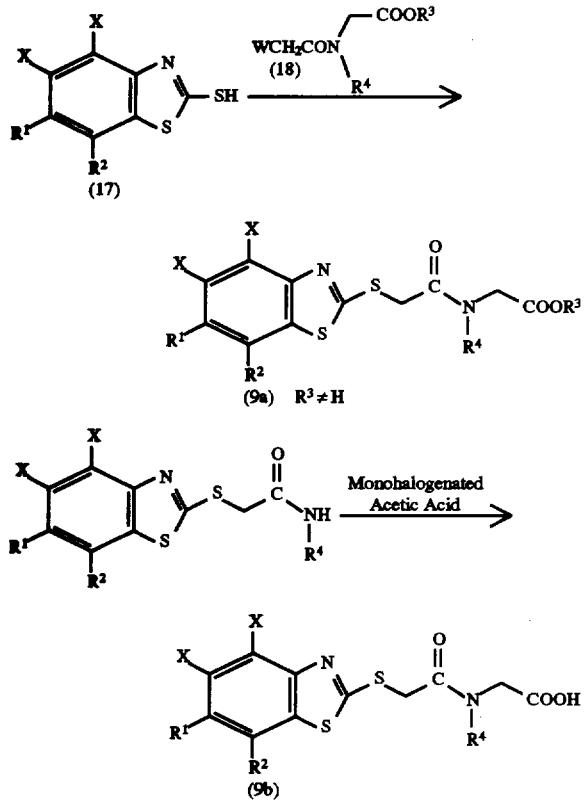

In Preparation Scheme 4, the ester compound of Formula (9) wherein Z is O (Compound (9a)) can be prepared by reacting an appropriate compound of Formula (17) wherein X, $R^1$ and $R^2$ are previously defined, with an appropriate compound of Formula (18) wherein $R^3$ and $R^4$ are previously defined and W is halogen, methanesulfonyl or p-toluenesulfonyl, provided that $R^3$ excludes H, in the presence of a suitable base, if necessary, under an inert gas atmosphere. The base used in the reaction includes alkali metal hydrides such as sodium hydride, alkaline earth metal hydrides such as calcium hydride, alkali metal hydroxides such as sodium hydroxide and potassium hydroxide, alkali metal carbonates such as sodium carbonate and potassium carbonate, alkali metal alkoxides such as sodium methoxide, sodium ethoxide and potassium t-butoxide, etc. Preferred halogens for the compound of Formula (18) are chlorine, bromine, and the like.

The above reaction is conducted in conventional solvents which are free from any adverse action on the reaction or a mixture thereof. Preferred examples of such solvents are N,N-dimethylformamide, tetrahydrofuran, dimethylsulfoxide, etc. The reaction temperature range is not limited to, but is preferably about 0° to 100° C.

The ester compound Formula (9a) can be obtained according to the the aforementioned step while a corresponding carboxylic acid of Formula (9b) can be prepared by reacting an appropriate compound of Formula (19) wherein X, $R^1$, $R^2$ and $R^4$ are previously defined, with a monohalogenated acetic acid such as monochloroacetic acid and monobromoacetic acid, in the presence of a suitable base, if necessary, under an inert gas atmosphere. The reaction between the compound of Formula (19) and the monohalogenated acetic acid is conducted in conventional solvents which are free from any adverse action on the reaction or a mixture thereof. Preferred examples of such solvents are N,N-dimethylformamide, dimethylsulfoxide, etc. The base used in the reaction includes alkali metal carbonates such as sodium carbonate and potassium carbonate, alkali metal alkoxides such as sodium methoxide, sodium ethoxide and potassium t-butoxide, etc. The reaction temperature range is not limited to, but is preferably about −20° C. to about 80° C.

(E) Preferred compounds of Formula (10)

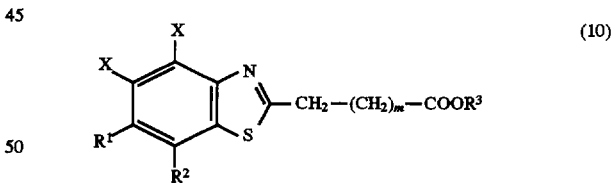

wherein X, $R^1$, $R^2$, $R^3$ and m are previously defined, can be prepared, for example, by the method described in Preparation Scheme 5.

Preparation Scheme 5

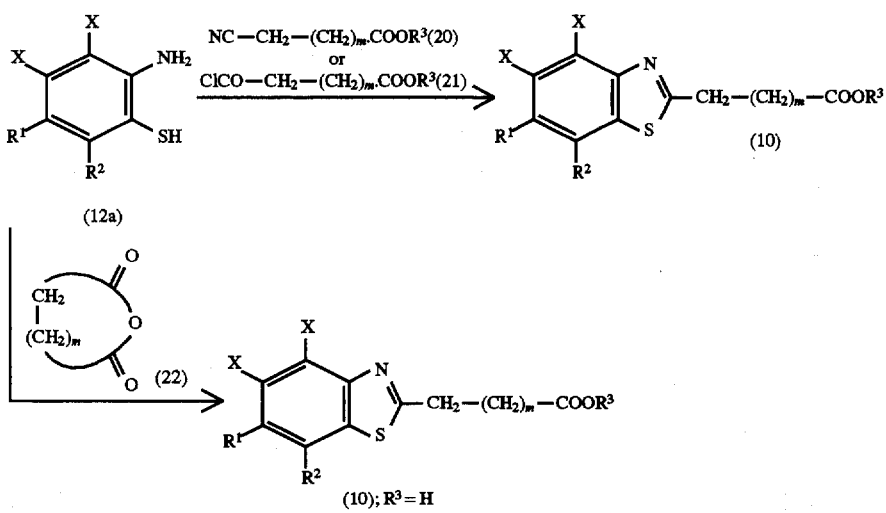

In Preparation Scheme 5, the compound of Formula (10) can be prepared by reacting an appropriate compound of Formula (12a) wherein X, $R^1$ and $R^2$ are previously defined, or an acid addition salt thereof, with an appropriate compound of Formula (20) wherein $R^3$ and m are previously defined, or Formula (21) wherein $R^3$ and m are previously defined, if necessary in the presence of a base, preferably under an inert gas atmosphere. The reaction may be conducted under the substantially same conditions as in the aforementioned Preparation Scheme 1 or 2. The ester product can be converted into a corresponding carboxylic acid by hydrolysis similar thereto.

The carboxylic acid compound of Formula (10) can be prepared by reacting an appropriate compound of Formula (12a) with an appropriate acid anhydride compound of Formula (22) wherein m is previously defined. The reaction is conducted in the presence of or in the absence of a solvent. When it is carried out in the solvent, it is convenient to use conventional solvents which are free from any adverse action on the reaction. Preferred examples of such solvents are N,N-dimethylformamide, N-methylpyrrolidone, etc. The reaction temperature range is not limited to, but is preferably room temperature to about 150° C.

(F) Preferred compounds of Formula (11)

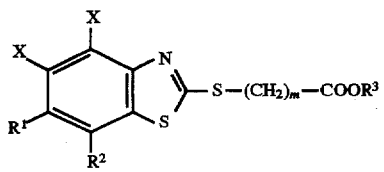
(11)

wherein X, $R^1$, $R^2$, $R^3$ and m are of the same meaning as defined above, can be prepared, for example, by the method described in Preparation Scheme 6.

Preparation Scheme 6

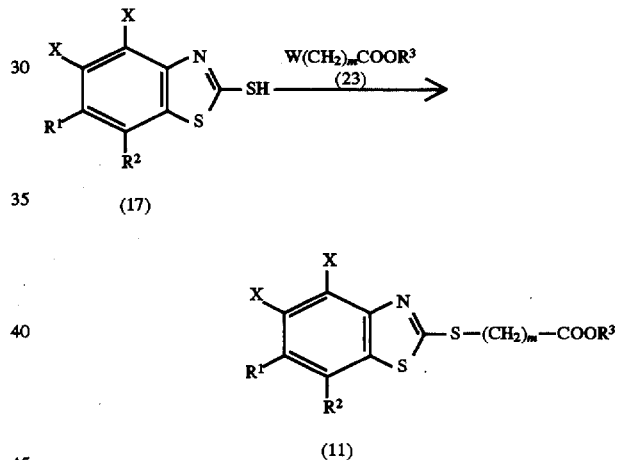

In Preparation Scheme 6, the compound of Formula (11) can be prepared by reacting an appropriate compound of Formula (17) wherein X, $R^1$ and $R^2$ are previously defined, with an appropriate compound of Formula (23) wherein $R^3$ and m are previously defined and W is halogen, methanesulfonyl or p-toluenesulfonyl, under the substantially same conditions as in the aforementioned Preparation Scheme 4i). The ester product can be converted into a corresponding carboxylic acid by hydrolysis similar thereto.

(G) Preferred compounds of Formula (26) wherein X, $R^1$, $R^2$, $R^3$ and Y are previously defined, can be prepared, for example, by the method described in Preparation Scheme 7.

Preparation Scheme 7

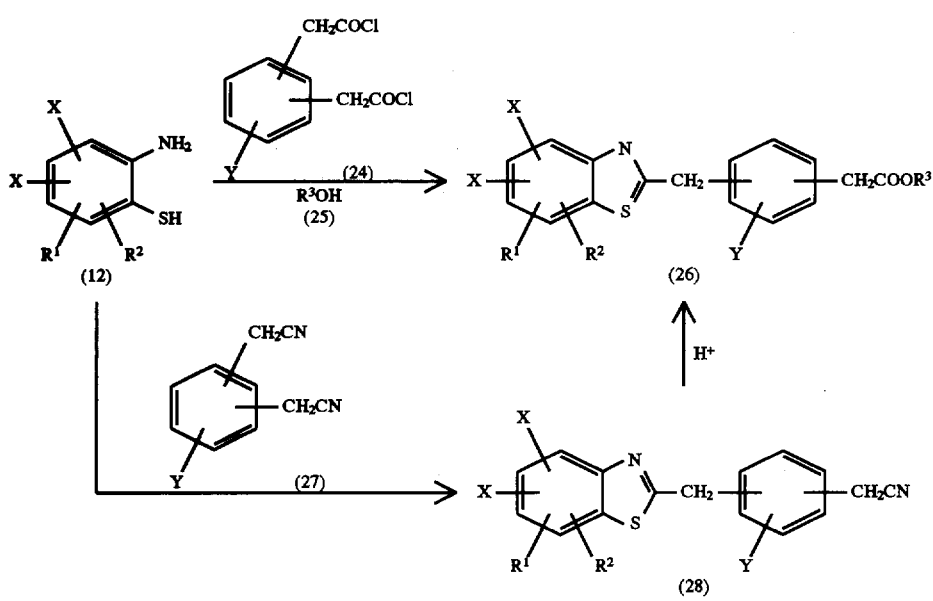

In Preparation Scheme 7, the compounds of Formula (26) can be prepared by reacting an appropriate compound of Formula (12) or an acid addition salt thereof, with an appropriate compound of Formula (24) wherein Y is previously defined, if necessary, in the presence of a base, preferably under an inert gas atmosphere, followed by reaction with an appropriate compound of Formula (25) wherein $R^3$ is previously defined. Preferred examples of the compound of Formula (25) include water, methanol, ethanol, etc. Preferred examples of solvents used in the reaction step wherein the compound of Formula (12) is reacted with the compound of Formula (24) are N-methylpyrrolidone, N, N-dimethylformamide, etc. The reaction temperature range is preferably ice cooling to about 100° C. When the compound of Formula (26) is an ester, it can be hydrolyzed to produce a corresponding carboxylic acid. The compound of Formula (12) or its acid addition salt can be condensed with the compound of Formula (27) wherein Y is previously defined to form the compound of Formula (28) wherein X, $R^1$, $R^2$ and Y are previously defined, which can be hydrolyzed to produce the compound of Formula (26). The reaction of the compound of Formula (12) with the compound of Formula (27) can be run, if necessary, in the presence of an appropriate acid, preferably under an inert gas atmosphere. The reaction may be conducted in the presence of or in the absence of an appropriate solvent. When it is conducted in solvents, it is often convenient to use conventional solvents which are free from any adverse action on the reaction. Preferred examples of such solvents are methanol, ethanol, propanol, etc. Preferred acids include, for example, inorganic acids such as hydrochloric acid, hydrobromic acid, sulphuric acid, nitric acid and phosphoric acid, organic acids such as formic acid and acetic acid, and the like. Among them, strong acids such as hydrochloric acid and sulphuric acid are preferable. The reaction temperature range is preferably about 60° C. to 200° C. The compounds of Formula (27) are known substances or ones which are readily producible by known techniques (e.g., Japanese Unexamined Patent Publication No. 19067/1989). Hydrolysis of the compound of Formula (28) can be conducted in an appropriate acid. Preferred examples of such acids are sulphuric acid, hydrochloric acid, hydrobromic acid, phosphoric acid, trifluoroacetic acid, etc. The hydrolysis can be conducted in conventional solvents or mixtures thereof which are free from any adverse action on the reaction. The reaction temperature range is not limited to but it can be run at temperatures within the range of 60° C. to reflux.

Among the compounds obtained by the aforementioned preparation schemes, the compounds of Formula (8):

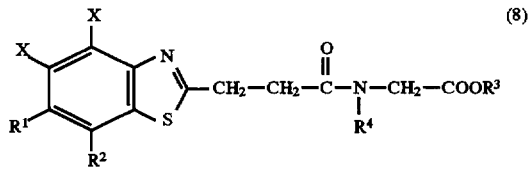

(8)

wherein X, Z, $R^1$, $R^2$, $R^3$ and $R^4$ are previously defined, comprises a mixture of geometric isomers (E) and (Z) attributed to a rotational barrier of the amide moiety. Such isomers can be resolved into each pure isomer by techniques known per se depending on necessity. Therefore, it is apparent that the compound of the present invention includes such geometric isomers.

The compound of the present invention can be separated, isolated and purified by conventional techniques including extraction, fractionation, chromatography, salting-out, crystallization, recrystallization, etc.

Another aspect of the present invention is to provide a pharmaceutical composition comprising an effective amount of the compound of Formula (1) or a pharmaceutically acceptable salt thereof. The pharmaceutical composition is useful in the prophylactic and therapeutic treatment of various diseases or symptoms associated with diabetes, even related to aldose reductases. Preferably the pharmaceutical composition is useful in the prophylactic and therapeutic treatment of diabetic complications including cataract, keratopathy, retinopathy peripheral and autonomic neuropathy, nephropathy and the like.

Still another aspect of the present invention is to provide a method for inhibiting aldose reductase and/or prophylactically and therapeutically treating diabetic complications of targets which comprises applying an effective amount of the compound of Formula (1) or a pharmaceutically acceptable salt thereof to said target.

Aldose reductase, which is a member of an aldo-keto reductase, converts glucose into sorbitol and widely exists in various tissues of human body. Aldose reductase and sorbitol dehydrogenase, which can oxidize sorbitol to fructose, act in the polyol pathway wherein glucose is converted into fructose through sorbitol. It is believed that in diabetes glucose entry into cells increases due to chronic hyperglycemia, glucose metabolism through the polyol pathway is activated, and polyols such as sorbitol are accumulated resulting in the development of various complications.

The compounds of the present invention potently inhibit aldose reductase activity and the accumulation of polyols such as sorbitol, which are considered to be related to the pathogenesis of diabetic complications. In view of their advantageous features, the compounds of the present invention are effective in the prophylactic and therapeutic treatment of various diabetic complications. Diabetic complications discussed herein include cataract, keratopathy, retinopathy, peripheral and autonomic neuropathy, nephropathy, and the like. The compounds of the present invention may be useful in the prophylactic and therapeutic treatment of theses complications because of their aldose reductase inhibiting activity and other activities.

The compounds of the present invention serving as aldose reductase inhibitors and prophylactic and therapeutic agents for preventing and treating diabetic complications can be used independently without any additives, but preferably in admixture of any of pharmaceutically acceptable additives. The compounds of the present invention may be orally, parenterally, ophthalmically, rectally, or topically administered as pharmaceutical compositions or formulations. Preferably it can be applied by various routes including oral routes, injection, or application to mucosa of eye, oral cavity or rectum. Preferred formulations for each administration route are as follows:

For oral administration, additives are any pharmaceutical ingredients as long as they are suitable for oral drugs and the intended purposes according to the present invention. Usually, the pharmaceutical additive is selected from conventional pharmaceutical components such as carriers, vehicles, adjuvants, excipients, diluents, binders, disintegrants, preservatives, antioxidants, sweetening, flavoring, perfuming, lubricating, thickening, buffering and coating agents. The oral formulations of the present invention include tablets, granules, fine granules, powders, syrups, capsules, etc.

For injection, the additives include pharmaceutical ingredients suitable for aqueous or non-aqueous injections. Usually, the additive is selected from conventional pharmaceutical components such as solubilizers, solution adjuvants, suspending agents, pH regulators and stabilizers. In addition, it may be selected from conventional ingredients suitable for preparing powders for injection, which are used in solution or suspension when administered.

For application to mucosa, such additives include pharmaceutical ingredients suitable for preparing aqueous or non-aqueous solutions, gels or ointments. Usually, the additive is selected from conventional pharmaceutical components such as solubilizers, solution adjuvants, suspending agents, emulsifying agents, buffering agents, stabilizers, preservatives, vaseline, purified lanolin, liquid paraffin, and Platisbase (Squibb & Sandoz, US).

Desired oral drugs, injections or drugs for mucosal applications comprising the compound of the present invention in admixture with the aforementioned ingredient can be prepared according to the manufacturing methods described in The 12th Pharmacopoeia of Japan (JPXII) or appropriately modified ones.

The pharmaceutical compositions (drugs) of the present invention are administered to mammals including human. These drugs of the present invention inhibit aldose reductase activity and the accumulation of sorbitol in tissues, as discussed above. In view of the unique features, they are effective in the prophylactic and therapeutic treatment of various diabetic complications that are difficult to prevent and treat only with euglycemic agents such as insulin and synthetic hypoglycemic agents.

The compounds and salts thereof according to the present invention are of low toxicity and clinically useful in prophylactically and therapeutically treating diseases or symptoms related to diabetes, for example, various diabetic complications. The doses of these compounds or salts thereof are usually 1 to 1,500 mg/day, preferably 5 to 1,000 mg/day for oral administration; usually 1 to 500 mg/day, preferably 3 to 300 mg/day for injection; and usually 1 to 500 mg/day, preferably 3 to 300 mg/day for application to mucosa.

Specific dose levels for any particular patient will be employed depending upon a variety factors including the activity of specific compounds employed, the age, body weight, general health, sex, diet, timing of administration, route of administration, rate of excretion, drug combination, and the severity of the particular disease or symptom undergoing therapy. The optimum dose is preferably determined based on how long the patient has suffered from diabetes, and the patient's age, sex, body weight and other factors.

The drugs of the present invention can be administered to patients developing diabetic complications such as cataract, keratopathy, retinopathy, peripheral or autonomic neuropathy, or nephropathy. Moreover, these drugs can be administered to the cases of diabetes without complications with the aim of prophylactically preventing them from developing. These drugs can be used independently, but, of course, can be used in combination with insulin or other antidiabetic agents (e.g., chlorpropamide, acetohexamide, tolbutamide, etc.).

Biological Experiment

The following is illustrative of experimental procedures for pharmacological tests and examples of typical results for various test compounds of Formula (1), which are provided to illustrate the efficacy of the compounds of Formula (1). Other compounds of the present invention that are not shown here also exert the same efficacy.

1 Aldose Reductase Inhibition
(Preparation of Enzyme)

Aldose reductase samples were prepared from porcine lens according the method by S. Hayman et al., (Journal of Biological Chemistry, 240, p. 877–882 (1965)).

In brief, lens of porcine eyes were frozen (−80° C.) until employed. These lenses were homogenized with distilled water and then centrifuged at 10,000×g for 15 minutes. The supernatant was fractionated with 0 to 40% ammonium sulfate and centrifuged at 10,000×g for 10 minutes. The resultant supernatant was dialyzed overnight against 0.05M sodium chloride. The dialyzed solution was used as an aldose reductase sample.
(Assay of Enzymatic Activity)

Aldose reductase activity was assayed according to the aforementioned method by S. Hayman et al.

In brief, to 200 µl of 40 mM phosphate buffer (pH 6.2) containing lithium sulfate, 0.4M (final concentration); NADPH (reduced nicotinamide adenine dinucleotide phosphate), 0.1 mM (final concentration); and DL-glyceraldehyde as a substrate, 3 mM (final concentration) was added 25 µl of the aldose reductase solution obtained by the aforementioned method and 25 µl of 1% DMSO solutions containing a sample inhibitor compound with different concentrations. The mixtures were incubated at 37° C. for 2 minutes for reaction and changes in the absorbance at 340 nm were read using an autoanalyzer (Hitachi Corporation, Model 7070, Japan). The change in the absorbance of a mixed solution including 1% DMSO instead of sample compounds was expresses as 100%. Table 1 shows the inhibiting activity of each sample compound. $IC_{50}(M)$ means the concentration of the compounds, required for 50% inhibition of aldose reductase activity.

TABLE 1

| Sample Compounds | $IC_{50}(M)$ |
|---|---|
| Example 1-ii) | $6.6 \times 10^{-9}$ |
| Example 3-iii) | $1.3 \times 10^{-8}$ |
| Example 4-ii) | $8.3 \times 10^{-9}$ |
| Example 5-ii) | $9.7 \times 10^{-9}$ |
| Example 6-ii) | $2.1 \times 10^{-8}$ |
| Example 7-ii) | $1.1 \times 10^{-8}$ |
| Example 8-ii) | $2.3 \times 10^{-8}$ |
| Example 15-ii) | $1.4 \times 10^{-8}$ |
| Example 19-ii) | $1.2 \times 10^{-8}$ |
| Example 20-ii) | $1.9 \times 10^{-8}$ |
| Example 21 | $6.7 \times 10^{-9}$ |
| Example 22-ii) | $9.6 \times 10^{-9}$ |
| Example 28-ii) | $9.4 \times 10^{-9}$ |
| Example 30-ii) | $8.7 \times 10^{-9}$ |
| Example 31-ii) | $6.7 \times 10^{-9}$ |
| Example 32-ii) | $8.4 \times 10^{-9}$ |

2) Inhibitory Effect on Sorbitol Accumulation in the Tissues of Experimental Diabetic Rats (Prophylactic effect)

Sprague-Dawley rats (male, 6-week-old, 5–6 rats/group), fasted for 18 hours, were made diabetic by a single intravenous (tail vein) injection of 60 mg/kg body weight of streptozotocin (Sigma). Four, eight and twenty four hours after the injection of streptozotocin, respectively, a sample compound suspended in 0.5% carboxymethyl cellulose was administered orally to the rats at a dose of 10 or 30 mg/kg. The rats were fed with diet and water ad libitum during the experiment. Three hours after the final administration, the sorbitol contents in the tissues (sciatic nerve, lens) was assayed enzymatically using SDH (sorbitol dehydrogenase) and NAD (β-nicotinamide adenine dinucleotide) according to the method by H. U. Bergmeyer et al. (Methods of Enzymatic Analysis, 3, p. 1323–1330 (1974)). The sorbitol contents in control groups to which 0.5% carboxymethyl cellulose was administered instead of sample compounds is expressed as 100%. Table 2 shows the result of the tests using the compounds of the present invention.

TABLE 2

| | Sorbitol Accumulation (%)[1] | |
|---|---|---|
| Sample Compounds[2] | Nerve | Lens |
| Example 1-ii) | 0** | 4** |
| Example 4-ii) | 46** | 20** |
| Example 20-ii) | 15** | 63 |
| Example 21 | 0** | 40** |
| Example 22-ii) | 0** | 41** |

**Tukey's Multiple Range Test: P < 0.01
[1]Control is expressed as 100%.
[2]The dose was 30 mg/kg in Examples 1-ii) and 4-ii), and 10 mg/kg in other examples.

3) Safety Study

The safety of the compounds of the present invention was confirmed according to the following experimental procedure.

Normal ICR mice (male, 7-week-old, 5 mice/group), fasted for 18 hours, received orally the compound each of Examples 1-ii), 5-ii), 19-ii), 21, 22-ii) and 23-ii) suspended in 0.5% carboxymethyl cellulose at a dose of 1000 mg/kg. Control groups received only 0.5% carboxymethyl cellulose orally. All were observed for the following 7 consecutive days. The mice were fed with diet and water ad libitum during the experiment. No animal died and body weight changes in treated animal groups were similar to that in control group.

4) Inhibitory Effect on Sorbitol Accumulation in the Tissues of Experimental Diabetic Rats (Therapeutic Effect)

Sprague-Dawley rats (male, 6-week-old, 5 to 6 rats/group), fasted for 18 hours, were made diabetic by injecting streptozotocin (Sigma) at a dose of 60 mg/kg body weight into the tail vein thereof. From 7 days after the streptozotocin injection, a sample compound suspended in 0.5% carboxymethyl cellulose was administered orally to the rats at a dose between 1 and 10 mg/kg once daily for 5 consecutive days. The rats were fed with diet and water ad libitum during the experiment. Three hours after the final administration, the sorbitol contents in the tissues (sciatic nerve, lens) was assayed enzymatically using SDH (sorbitol dehydrogenase) and NAD (β-nicotinamide adenine dinucleotide) according to the method by H. U. Bergmeyer et al. (Methods of Enzymatic Analysis, 3, p. 1323–1330 (1974)). The sorbitol contents in control groups to which 0.5% carboxymethyl cellulose was administered instead of sample compounds is expressed as 100%.

TABLE 3

| | Dose Level | Sorbitol Accumulation (%)[1] | |
|---|---|---|---|
| Sample Compounds | (mg/kg) | Nerve | Lens |
| Example 1-ii) | 10 | 2** | 68 |
| Example 22-ii) | 3 | 2** | 25** |
| Example 24-ii) | 10 | 11** | 26** |
| Example 25-ii) | 1 | 0** | 47 |
| Example 31-ii) | 3 | 1** | 77 |

**Tukey's Multiple Range Test: P < 0.01
[1]Control is expressed as 100%.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1 i) To a solution of monomethyl 1,3-phenylene diacetate (531 mg, 2.6 mmol) in benzene (5 ml) was gradually added thionyl chloride (607 mg, 5.2 mmol). The mixture was heated to reflux for 2 hours. An excess of thionyl chloride was then distilled off in vacuo leaving 3-methoxycarbonylmethylphenylacetyl chloride. 2-Amino-3,4,6-trifluorothiophenol (507 mg, 2.8 mmol) was dissolved in N-methylpyrrolidone (NMP, 5 ml) under a nitrogen stream. To the resultant solution was gradually added the product 3-methoxycarbonylmethylphenylacetyl chloride thus obtained and the mixture was stirred at 100° C. for 2 hours. After cooling, the reaction mixture was diluted with water and extracted with ethyl acetate. The organic layer was dried and then evaporated to yield a residue, which was purified on a silica gel column to give methyl 3-[(4,5,7-trifluorobenzothiazol-2-yl)methyl]phenylacetate (267 mg, 27%) as an oil.

NMR(CDCl$_3$) δ:3.64(2H,s), 3.70(3H,s), 4.45(2H,s), 6.9–7.1(1H,m), 7.2–7.4(4H,m)

MS:351(M$^+$), 291,277 ii) To a solution of methyl 3-[(4,5,7-trifluorobenzothiazol-2-yl)methyl]phenylacetate (231 mg, 0.66 mmol) in a mixture of water (5 ml) and dioxane (5 ml) was added dropwise 2N sodium hydroxide (2 ml, 4 mmol). After the addition was complete, the mixture was stirred for 2 hours, then diluted with water, washed with ether, acidified with 10% hydrochloric acid and extracted with ethyl acetate. The organic layer was dried, then evaporated to yield a residue, which was recrystallized from isopropyl ether to give 3-[(4,5,7-trifluorobenzothiazol-2-yl)methyl]phenylacetic acid (134 mg, 90%) as a colorless powder. m.p. 132° to 134° C.

NMR(CDCl$_3$) δ:3.67 (2H,s), 4.45 (2H,s), 6.9–7.1 (1H,m), 7.2–7.4 (4H,m)

MS:337 (M$^+$), 293,277

Example 2 i) A solution of ethyl 3-iodobenzoate (2 g, 7.2 mmol), palladium acetate (16 mg, 0.072 mmol), triethylamine (729 mg, 7.2 mmol) and acrylonitrile (480 mg, 9.0 mmol) in acetonitrile (10 ml) was stirred at reflux for 3 hours under a nitrogen stream. After additional palladium acetate (16 mg, 0.072 mmol) was added to the reaction mixture, the resulting mixture was stirred at reflux for 9 hours. The reaction mixture was diluted with water and extracted with ethyl acetate. The organic layer was washed with a saturated saline solution, then dried and evaporated to yield a residue, which was purified on a silica gel column to give ethyl 3-(2-cyanovinyl)benzoate (808 mg, 55%) as an oil mixture of E and Z isomers (E:Z=3:1).

NMR(E:Z=3:1)(CDCl$_3$) δ:1.42 (3H,t,J=7.3 Hz), 4.41 (2H, q,J=7.3 Hz), 5.98 (5.54) (1H,d,Jtrans=16.8 Hz,Jcis=12.6 Hz), 7.45 (7.24) (1H,d,Jtrans=16.8 Hz, Jcis=12.6 Hz), 7.50 (7.55) (1H,dd,J=8.0 Hz and 7.7 Hz), 7.63 (1H,d,J=7.7 Hz), 8.11 (8.16) (1H,d,J=8.0 Hz), 8.14 (8.31) (1H,s)

ii) To a solution of ethyl 3-(2-cyanovinyl)benzoate (800 mg, 4.0 mmol) in methanol (30 ml) was added cautiously 10% palladium/C and the mixture was stirred at 3 atm. for 10 hours under a hydrogen atmosphere. After the mixture was filtered to remove a solid, the filtrate was evaporated to yield ethyl 3-(2-cyanoethyl)benzoate (682 mg, 84%) as a colorless oil.

NMR(CDCl$_3$) δ:1.40 (3H,t,J=7.3 Hz), 2.67 (1H,t,J=7.3 Hz), 3.02 (1H,t, J=7.3 Hz), 4.39 (2H,q,J=7.3 Hz), 7.3–7.5 (2H,m), 7.91 (1H,s), 7.96 (1H,d,J=6.3 Hz)

iii) To a solution of zinc chloride (26 mg, 0.19 mmol) in chlorobenzene (3 ml) was added a solution of 2-amino-3,4,6-trifluorothiophenol hydrochloride (269 mg, 1.2 mmol) in chlorobenzene (1 ml) and a solution of ethyl 3-(2-cyanoethyl)benzoate (254 mg, 1.2 mmol) in chlorobenzene (1 ml) and the mixture was heated to reflux for 40 hours. The reaction mixture was evaporated followed by addition of methylene chloride. The resulting mixture was washed with water, dried and evaporated to yield a residue, which was purified on a silica gel column to give ethyl 3-[2-(4,5,7-trifluorobenzothiazol-2-yl)ethyl]benzoate (133 mg, 30%) as an oil.

NMR(CDCl$_3$) δ:1.40 (t, 3H,J=7.2 Hz), 3.28 (t, 2H,J=7.8 Hz), 3.48 (t, 2H, J=7.8 Hz), 4.38 (q,2H,J=7.2 Hz), 6.9–7.1 (1H,m), 7.37 (br.t, 1H,J=7.6 Hz), 7.43 (br.d, 1H,J=7.6 Hz), 7.92 (br.d, 1H,J=7.6 Hz), 7.95 (1H,s)

iv) To a solution of ethyl 3-[2-(4,5,7-trifluorobenzothiazol-2-yl)ethyl]benzoate (133 mg, 0.36 mmol) in a mixture of water (5 ml) and dioxane (5 ml) was added dropwise aqueous 2N sodium hydroxide (2 ml) and the mixture was stirred for 7 hours at ambient temperature. The reaction mixture was diluted with water and then washed with ether. The aqueous layer was acidified with 10% hydrochloric acid and extracted with ethyl acetate. After drying, evaporation of the solvent left crude crystals, which were recrystallized from ether to give 3-[2-(4,5,7-trifluorobenzothiazol-2-yl)ethyl]benzoic acid (82 mg, 68%) as colorless crystals.

m.p.190° C. (dec.)

NMR(CDCl$_3$) δ:3.31 (2H,t,J=7.6 Hz), 3.51 (2H,t,J=7.6 Hz), 6.9–7.1 (1H,m), 7.42 (1H,t,J=7.6 Hz), 7.50 (1H,d,J=7.6 Hz), 8.00 (1H,d,J=7.6 Hz), 8.03 (1H,s)

MS:337 (M$^+$), 319,291,216,135

Example 3 i)
Method A

To NMP (6 ml) was added 2-amino-3,4,6-trifluorothiophenol (1.61 g, 9 mmol) and ethyl succinyl chloride (1.48 g, 9 mmol) and the mixture was heated and stirred for 1 hour at 100° C. under a nitrogen stream. The reaction solution was poured into ice-water and extracted with ethyl acetate. The organic layer was washed with water, then dried and evaporated to yield a residue, which was purified on a silica gel column to give ethyl 3-(4,5,7-trifluorobenzothiazol-2-yl)propionate (1.12 g, 43%) as an oil.

To a mixture of methanol (8 ml), water (6 ml) and 2N sodium hydroxide (2 ml, 4 mmol) was added ethyl 3-(4,5,7-trifluorobenzothiazol-2-yl)propionate (1.1 g, 3.8 mmol) and the mixture was stirred for 15 min. at ambient temperature. The reaction solution was diluted with water and then extracted with ethyl acetate. The organic layer was washed with water, then dried and evaporated to yield a residue, which was recrystallized from hexane-isopropyl ether to give 3-(4,5,7-trifluorobenzothiazol-2-yl)propionic acid (840 mg, 85%) as colorless needles.

m.p.123° to 125° C.

NMR(CDCl$_3$) δ:3.06 (2H,t,J=7.1 Hz), 3.46 (2H,t,J=7.1 Hz), 6.98–7.09 (1H,m)

Method B

To a solution of 2-amino-3,4,6-trifluorothiophenol (1.79 g, 10 mmol) in NMP (5 ml) was added dropwise a solution of succinic anhydride (1.0 g, 10 mmol) in NMP (5 ml) at ambient temperature under a nitrogen stream and the mixture was heated to 100° C. for 1 hour. The resultant mixture was basified by dilution with aqueous sodium carbonate and washed with ether. The aqueous layer was acidified with 7% hydrochloric acid and extracted with ethyl acetate. The organic layer was washed with water, then dried and evaporated to yield crude crystals, which were washed with hexane-isopropyl ether to give 3-(4,5,7-trifluorobenzothiazol-2-yl)propionic acid 2.16 g, 83%).

ii) To methylene chloride (10 ml) was added sarcosine ethyl ester hydrochloride (307 mg, 2 mmol), 1-(3-dimethylaminopropyl)-3-ethylcarbodiimide hydrochloride (WSC.HCl; 422 mg, 2.2 mmol), 3-(4,5,7-trifluorobenzothiazol-2-yl)propionic acid (522 mg, 2 mmol) and triethylamine (220 mg, 2.2 mmol), and the mixture was stirred at room temperature for 15 hours. The resulting mixture was washed with water, dried and evaporated to yield a residue, which was purified on a silica gel column to give N-[3-(4,5,7-trifluorobenzothiazol-2-yl)propionyl]-N-methylglycine ethyl ester (610 mg, 85%) as an oil.

NMR(CDCl$_3$) δ:1.26 (1.29) (3H,t,J=7.2 Hz), 3.06 (2.92) (2H,t, J=6.9 Hz), 3.13 (3.00) (3H,s), 3.45 (2H,t,J=6.9 Hz), 4.13 (4.10) (2H,q,J=7.2 Hz), 6.95–7.06 (1H,m)

It is deduced that the product is a mixture of E and Z isomers (E:Z ratio=4:1; estimated by NMR).

MS:360 (M$^+$), 243,215 iii) To a solution of N-[3-(4,5,7-trifluorobenzothiazol-2-yl)propionyl]-N-methylglycine ethyl ester (290 mg, 0.8 mmol) in methanol (2 ml) was added 2N sodium hydroxide (0.5 ml, 1 mmol) and the mixture was stirred for 30 min. at room temperature. The reaction mixture was diluted with water and then washed with ether. The aqueous layer was acidified with 7% hydrochloric acid and extracted with ethyl acetate. The organic layer was washed with water, then dried and evaporated to yield a residue, which was recrystallized from ethanol-isopropyl ether to give N-[3-(4,5,7-trifluorobenzothiazol-2-yl)propionyl]-N-methylglycine (185 mg, 70%).

m.p.138° to 140° C.

NMR(CDCl$_3$) δ:3.08 (2.98) (2H,t,J=6.9 Hz), 3.16 (3.01) (3H,s), 3.50 (2H,t,J=6.9 Hz), 4.18 (4.15) (2H,s), 6.95–7.06 (1H,m)

It is deduced that the product is a mixture of E and Z isomers (E:Z ratio=4:1; estimated by NMR).

MS:348 (M$^+$), 216

Example 4 i) To a solution of 3-(4,5,7-trifluorobenzothiazol-2-yl)propionic acid (522 mg, 2 mmol) obtained in Example 3-i) in a mixture of toluene (5 ml) and N,N-dimethylformamide (DMF; 1 ml) was added thionyl chloride (357 mg, 3 mmol) and the mixture was stirred for 1 hour at room temperature. To the ice cold reaction mixture was N-phenylglycine methyl ester hydrochloride (403 mg, 2 mmol) and triethylamine (400 mg, 4 mmol) and the mixture was stirred for 2 hours. The reaction mixture was diluted with water and then extracted with ethyl acetate. The organic layer was washed with water, then dried and evaporated to yield a residue, which was purified on a silica gel column to give N-[3-(4,5,7-trifluorobenzothiazol-2-yl)propionyl]-N-phenylglycine methyl ester (240 mg, 29%) as an oil.

NMR(CDCl$_3$) δ:2.78 (2H,t,J=6.9 Hz), 3.44 (2H,t,J=6.9 Hz), 3.73 (3H, s), 4.40 (2H,s), 6.93–7.03 (1H,m), 7.3–7.5 (5H,m)

MS:408 (M$^+$), 244,215 ii) To a solution of N-[3-(4,5,7-trifluorobenzothiazol-2-yl)propionyl]-N-phenylglycine methyl ester (420 mg, 1 mmol) in a mixture of water (3 ml) and dioxane (6 ml) was added dropwise 2N sodium hydroxide (1.2 ml) with stirring under ice cooling and the mixture was stirred for 1 hour at room temperature. The reaction mixture was then diluted with water and washed with ether. The aqueous layer was acidified with 7% hydrochloric acid and extracted with ethyl acetate. The organic layer was washed with water, then dried and evaporated to yield a residue, which was recrystallized from ethyl acetate-isopropyl ether to give N-[3-(4,5,7-trifluorobenzothiazol-2-yl)propionyl]-N-phenylglycine 210 mg, 52%) as a colorless powder.

m.p.121° to 124° C.

NMR(CDCl$_3$) δ:2.77 (2H,t,J=6.8 Hz), 3.43 (2H,t,J=6.8 Hz), 4.41 (2H,s), 6.93–7.03 (1H,m), 7.3–7.5 (5H,m)

MS:394 (M$^+$), 376,245,244

Example 5 i) To methylene chloride (10 ml) was added 3-(4,5,7-trifluorobenzothiazol-2-yl)propionic acid (522 mg, 2 mmol) obtained in Example 3-i), WSC.HCl (422 mg, 2.2 mmol) and N-benzylglycine ethyl ester (386 mg, 2 mmol) and the mixture was stirred for 15 hours at room temperature. The reaction mixture was washed with 7% hydrochloric acid and water successively. The organic layer was dried and evaporated. The resulting residue was purified on a silica gel column to give N-benzyl-N-[3-(4,5,7-trifluorobenzothiazol-2-yl)propionyl]-glycine ethyl ester (680 mg, 78%) as an oil.

NMR(CDCl$_3$) δ:1.23 (3H,t,J=7.1 Hz), 3.16 (2.98) (2H,t, J=6.6 Hz), 3.53 (3.56) (2H,t,J=6.6 Hz), 4.04 (4.03) (2H,s), 4.16 (2H,q,J=7.1 Hz), 4.69 (4.67) (2H,s), 6.95–7.05 (1H,m), 7.2–7.4 (5H,m)

It is deduced that the product is a mixture of E and Z isomers (E:Z ratio=2:1; estimated by NMR).

MS:436 (M$^+$), 244,216,192 ii) N-Benzyl-N-[3-(4,5,7-trifluorobenzothiazol-2-yl)propionyl]-glycine ethyl ester (650 mg, 1.5 mmol) was treated according to the procedure for Example 4-ii) and the resultant product was recrystallized from isopropyl ether to give N-benzyl-N-[3-(4,5,7-trifluorobenzothiazol-2-yl)propionyl]glycine (535 mg, 87%) as a colorless powder.

m.p.144° to 146° C.

NMR(CDCl$_3$) δ:3.17 (2.98) (2H,t,J=6.9 Hz), 3.53 (3.56) (2H,t, J=6.9 Hz), 4.08 (4.06) (2H,s), 4.70 (4.67) (2H,s), 6.95–7.06 (1H,m), 7.15–7.45 (5H,m)

It is deduced that the product is a mixture of E and Z isomers (E:Z ratio=3:1; estimated by NMR).

MS:408 (M$^+$), 244,216,164

Example 6 i) The procedure of Example 5-i) was repeated replacing the glycine ester with N-phenethylglycine ethyl ester (414 mg, 2 mmol) and the resultant product was recrystallized from ethyl acetate-hexane to give N-[3-(4,5,7-trifluorobenzothiazol-2-yl)propionyl]-N-phenethylglycine ethyl ester (680 mg, 76%) as a colorless powder.

m.p.78° to 81° C.

NMR(CDCl$_3$) δ:1.25 (1.27) (3H,t,J=7.2 Hz), 2.78–2.98 (4H,m), 3.39 (3.50) (2H,t,J=6.9 Hz), 3.65 (3.62) (2H,t,J=6.9 Hz), 4.02 (3.93) (2H,s), 4.17 (4.20) (2H,q,J=7.2 Hz), 6.95–7.05 (1H,m), 7.15–7.35 (5H,m)

It is deduced that the product is a mixture of E and Z isomers (E:Z ratio=7:3; estimated by NMR).

MS:450 (M$^+$), 244,216 ii) N-[3-(4,5,7-trifluorobenzothiazol-2-yl)propionyl]-N-phenethylglycine ethyl ester (225 mg, 0.5 mmol) was treated according to the procedure for Example 4-ii) to obtain N-[3-(4,5,7-trifluorobenzothiazol-2-yl)propionyl]-N-phenethylglycine (185 mg, 88%) as a colorless powder.

m.p.139° to 140° C.

NMR(CDCl$_3$) δ:2.76–2.95 (4H,m), 3.38 (3.51) (2H,t,J= 6.9 Hz), 3.67 (3.64) (2H,t,J=6.9 Hz), 4.06 (3.96) (2H,s), 6.95–7.05 (1H,m), 7.1–7.35 (5H,m)

It is deduced that the product is a mixture of E and Z isomers (E:Z ratio=9:2; estimated by NMR).

MS :331,318,244

Example 7 i) To benzene (10 ml) was added N-[3-(4,5,7-trifluorobenzothiazol-2-yl)propionyl]-N-methylglycine ethyl ester (610 mg, 1.7 mmol) obtained in Example 3-ii) and phosphorus pentasulfide (378 mg, 1.7 mmol) and the mixture was heated at 60° C. for 3 hours. The organic phase was decanted and the residue was extracted with ether. All the organic phases were combined, washed with water, dried and evaporated to yield a residue, which was crystallized from hexane-isopropyl ether to give N-[3-(4,5,7-trifluorobenzothiazol-2-yl)-1-thioxopropyl]N-methylglycine ethyl ester (225 mg, 35%) as colorless crystals.

m.p.83° to 85° C.

NMR(CDCl$_3$) δ:1.28 (1.32) (3H,t,J=6.9 Hz), 3.33 (3.21) (2H,t, J=6.9 Hz), 3.45 (3.51) (3H,s), 3.75 (3.78) (2H,t, J=6.9 Hz), 4.24 (4.27) (2H,q,J=6.9 Hz), 4.76 (4.52) (2H,s), 6.96–7.06 (1H,m)

It is deduced that the product is a mixture of E and Z isomers (E:Z ratio=4:1; estimated by NMR).

MS:376 (M$^+$), 259,227,216 ii) To a solution of N-[3-(4,5,7-trifluorobenzothiazol-2-yl)-1-thioxopropyl]-N-methylglycine ethyl ester (190 mg, 0.5 mmol) in a mixture of water (3 ml) and dioxane (6 ml) was added dropwise 2N sodium hydroxide (0.6 mmol) with stirring under ice-cooling and the mixture was stirred for 1 hour at room temperature, then diluted with water and washed with ether. The aqueous phase was acidified with 7% hydrochloric acid and extracted with ethyl acetate. The organic layer was washed with water, dried and then evaporated to yield a residue, which was crystallized from isopropyl ether to give N-[3-(4,5,7-trifluorobenzothiazol-2-yl)-1-thioxopropyl]-N-methylglycine (155 mg, 88%) as a pale brown powder.

m.p.150° to 152° C.

NMR(CDCl$_3$) δ:3.32 (3.21) (2H,t,J=6.8 Hz), 3.45 (3.50) (3H,s), 3.74 (3.71) (2H,t,J=6.8 Hz), 4.75 (4.52) (2H,s), 7.07–7.17 (1H,m)

It is deduced that the product is a mixture of E and Z isomers (E:Z ratio=4:1; estimated by NMR).

MS:348 (M$^+$), 216

Example 8 i) N-Benzyl-N-[3-(4,5,7-trifluorobenzothiazol-2-yl) propionyl]glycine ethyl ester (700 mg, 1.6 mmol; Example 5-i)) was treated according to the procedure for Example 7-i) and the resultant product was crystallized from ethyl acetate-hexane to give N-benzyl-N-[3-(4,5,7-trifluorobenzothiazol-2-yl)-1-thioxopropyl]glycine ethyl ester (330 mg, 46%) as a colorless powder.

m.p.86° to 88° C.

NMR(CDCl$_3$) δ:1.23 (1.26) (3H,t,J=7.2 Hz), 3.43 (3.27) (2H,t,J=6.7 Hz), 3.79 (3.85) (2H,t,J=6.7 Hz), 4.19 (4.20) (2H, q,J=7.2 Hz), 4.62 (4.45)(2H,s), 5.03 (5.39)(2H,s), 5.94–7.04 (1H,m), 7.1–7.5 (5H,m)

It is deduced that the product is a mixture of E and Z isomers (E:Z ratio=3:1; estimated by NMR).

MS:452 (M$^+$), 259,227,216 ii) N-Benzyl-N-[3-(4,5,7-trifluorobenzothiazol-2-yl)-1-thioxopropyl]glycine ethyl ester (220 mg, 0.5 mmol) was treated according to the procedure for Example 7-ii) and the resultant product was crystallized from ethyl acetate-hexane to give N-benzyl-N-[3-(4,5,7-trifluorobenzothiazol-2-yl)-1-thioxopropyl]glycine (170 mg, 80%) as a colorless powder.

m.p.138° to 140° C.

NMR(CDCl$_3$) δ:3.44 (3.29) (2H,t,J=6.8 Hz), 3.80 (3.84) (2H,t, J=6.8 Hz), 4.68 (4.51) (2H,s), 5.03 (5.39) (2H,s), 6.96–7.06 (1H,m), 7.1–7.5 (5H,m)

It is deduced that the product is a mixture of E and Z isomers (E:Z ratio=4:1; estimated by NMR).

MS:424 (M$^+$), 408,391,315

Example 9 i) To methylene chloride (20 ml) was added N-phenylglycine methyl ester (2.02 g, 10 mmol) and pyridine (1.58 g, 20 mmol) and the mixture was stirred. To the mixture was added dropwise a solution of chloroacetyl chloride (1.13 g, 10 mmol) in methylene chloride (3 ml) at room temperature and the resulting mixture was stirred for 15 hours, washed with water, dried and evaporated. The resultant residue was crystallized from isopropyl ether to give N-chloroacetyl-N-phenylglycine methyl ester (1.67 g, 70%) as a colorless powder.

TLC(CH$_2$Cl$_2$:MeOH=19:1) Rf=0.75 ii) To dimethylsulfoxide (DMSO; 6 ml) was added 4,5,7-trifluoro-2-mercaptobenzothiazole (442 mg, 2 mmol), N-chloroacetyl-N-phenylglycine methyl ester (479 mg, 2 mmol), calcium carbonate (276 mg, 2 mmol) and potassium iodide (20 mg) and the mixture was stirred at room temperature for 1 hour. The resultant reaction mixture was diluted with water, acidified with 7% hydrochloric acid and extracted with ethyl acetate. The organic layer was washed with water, dried and then evaporated to yield a residue, which was crystallized from isopropyl ether to give N-[2-(4,5,7-trifluorobenzothiazol-2-ylthio)acetyl]-N-phenylglycine methyl ester (700 mg, 82%) as a colorless powder.

m.p.145° to 147° C.

NMR(CDCl$_3$) δ:3.74 (3H,s), 4.08 (2H,s), 4.44 (2H,s), 6.88–6.99 (1H,m), 7.39–7.60 (5H,m)

Example 10 i) To DMSO (15 ml) was added α-chloroacetoanilide (850 mg, 5 mmol), 4,5,7-trifluoro-2-mercaptobenzothiazole (1.1 g, 5 mmol), potassium carbonate (690 mg, 5 mmol) and potassium iodide (50 mg) and the mixture was stirred at room temperature for 4 hours. The resultant reaction mixture was diluted with water, acidified with 7% hydrochloric acid and extracted with ethyl acetate. The organic layer was washed with water, dried and then evaporated to yield a crude product, which was purified on a silica gel column to give 2-(4,5,7-trifluorobenzothiazol-2-ylthio)-N-phenylacetamide (0.97 g, 52%).

NMR(CDCl$_3$) δ:4.09 (2H,s), 6.99–7.10 (1H,m), 7.10 (1H, t), 7.32 (2H,dd), 7.57 (2H,d), 9.55 (1H,bs)

ii) To DMSO (5 ml) was added 2-(4,5,7-trifluorobenzothiazol-2-ylthio)-N-phenylacetamide (354 mg, 1 mmol), bromoacetic acid (278 mg, 2 mmol) and potassium carbonate (414 mg, 3 mmol) and the mixture was stirred at room temperature for 5 hours under a nitrogen stream. The resultant reaction mixture was diluted with water and washed with ethyl acetate. The aqueous phase was acidified with 7% hydrochloric acid and extracted with ethyl acetate. The organic phase was washed with water, dried and then evaporated to yield crude crystals, which were recrystallized from ethyl acetate-hexane to give N-[2-(4,5,7-trifluorobenzothiazol-2-ylthio)acetyl]-N-phenylglycine (80 mg, 19%) as slightly yellow crystals.

m.p.174° to 176° C.

NMR(CDCl$_3$) δ:3.40 (2H,s), 4.10 (2H,s), 6.71–6.82 (1H, m), 7.40–7.60 (5H,m)

MS:412 (M$^+$), 394,368,367

Example 11

2-Amino-3,4,6-trifluorothiophenol (200 mg, 1.1 mmol) was dissolved in N-methylpyrrolidone (NMP, 1 ml) under a nitrogen stream. To the resultant solution was gradually added glutaric acid (127 mg, 1.1 mmol) at room temperature and the mixture was stirred at 100° C. for 6 hours. After naturally cooling, the mixture was diluted with water and extracted with ethyl acetate. The organic phase was washed with aqueous sodium bicarbonate. The alkaline phase was acidified with 10% hydrochloric acid and re-extracted with ethyl acetate. The combined organic phases were dried and then evaporated to yield a residue, which was recrystallized from acetonitrile to give 4-(4,5,7-trifluorobenzothiazol-2-yl)butanoic acid (133 mg, 44%).

m.p.113° to 114° C.

NMR(CDCl$_3$) δ:2.26 (2H,tt,J=7.6 Hz and 7.3 Hz), 2.56 (2H,t, J=7.3 Hz), 3.25 (2H,t,J=7.6 Hz), 6.9–7.1 (1H,m)

MS:275 (M$^+$), 257,216

Example 12

A solution of adipic acid (10.0 g, 68 mmol) in acetic anhydride (50 ml) was heated to reflux for 3 hours. An excess of acetic anhydride was then distilled off in vacuo leaving adipic anhydride (7.4 g). 2-Amino-3,4,6-trifluorothiophenol (200 mg, 1.1 mmol) was dissolved in NMP (1 ml) under a nitrogen stream. To the resultant solution was gradually added adipic anhydride (143 mg, 1.1 mmol) and the mixture was stirred at 100° C. for 6 hours. After naturally cooling, the mixture was diluted with water and extracted with ethyl acetate. The organic phase was extracted with aqueous sodium bicarbonate. The alkaline phase was acidified with 10% hydrochloric acid and re-extracted with ethyl acetate. The combined organic phases were dried and then evaporated to yield a residue, which was recrystallized from acetonitrile to give 5-(4,5,7-trifluorobenzothiazol-2-yl)pentanoic acid (81 mg, 26%).

m.p.122° to 124° C.

NMR(CDCl$_3$) δ:1.7–1.9 (1H,m),1.9–2.2 (1H,m), 2.45 (2H,t,J=7.2 Hz), 3.18 (2H,t,J=7.4 Hz), 6.9–7.1 (1H,m)

MS:289 (M$^+$), 216

Example 13 i) To xylene (6 ml) was added 2-amino-3,4,6-trifluorothiophenol hydrochloride (647 mg, 3 mmol), 6-cyanohexanoic acid ethyl ester (507 mg, 3 mmol) and ethanol (0.5 ml) and the mixture was heated to reflux for 60 hours under a nitrogen stream. The resultant reaction mixture was washed with water, dried and then evaporated to yield a residue, which was purified on a silica gel column to give 6-(4,5,7-trifluorobenzothiazol-2-yl)hexanoic acid ethyl ester (395 mg, 40%) as an oil.

NMR(CDCl$_3$) δ:1.25 (3H,t,J=7.1 Hz), 1.46–1.98 (6H,m), 2.33 (2H,t, J=7.3 Hz), 3.15 (2H,t,J=7.4 Hz), 4.12 (2H,q,J= 7.1 Hz), 6.95–7.06 (1H,m)

MS:331 (M$^+$), 203 ii) To methanol (3 ml) was added 6-(4,5,7-trifluorobenzothiazol-2-yl)hexanoic acid ethyl ester (390 mg, 1.18 mmol) and aqueous 2N sodium hydroxide (0.7 ml, 1.4 mmol) and the mixture was stirred at room temperature for 1 hour. The resultant reaction mixture was diluted with water and washed with ether. The aqueous phase was acidified with 7% hydrochloric acid and extracted with ethyl acetate. The organic phase was washed with water, dried and then evaporated to yield a residue, which was crystallized from hexane-isopropyl ether to give 6-(4,5,7-trifluorobenzothiazol-2-yl)hexanoic acid (170 mg, 48%) as a colorless powder.

m.p.84° to 86° C.

NMR(CDCl$_3$) δ:1.45–1.98 (6H,m), 2.39 (2H,t,J=7.3 Hz), 3.16 (2H,t, J=7.8 Hz), 6.95–7.06 (1H,m)

MS:303 (M$^+$), 203,167

Example 14 i) Monomethyl suberiate (500 mg, 2.7 mmol) was dissolved in benzene (5 ml). To the resulting benzene solution was gradually added thionyl chloride (632 mg, 5.4 mmol) at room temperature and the mixture was heated to reflux for 2 hours. After an excess of thionyl chloride was distilled off in vacuo, the resultant reaction mixture was gradually added to a solution of 2-amino-3,4,6-trifluorothiophenol (500 mg, 2.8 mmol) in NMP (5 ml) at room temperature and the mixture was heated with stirring at 100° C. for 23 hours under a nitrogen stream. After naturally cooling, the resultant solution was diluted with water and extracted with ethyl acetate. The organic layer was dried and then evaporated to yield a residue, which was purified on a silica gel column to give 7-(4,5,7-trifluorobenzothiazol-2-yl)heptanoic acid methyl ester (407 mg, 46%) as an oil.

NMR(CDCl$_3$) δ:1.2–1.6 (4H,m), 1.6–1.8 (2H,m), 1.8–2.0 (2H,m), 2.31 (2H,br.t,J=5.5 Hz), 3.14 (2H,br.t,J=6.3 Hz), 3.67 (3H,s), 6.9–7.1 (1H,m)

MS:331 (M$^+$), 258,216,202 iii) To a solution of 7-(4,5,7-trifluorobenzothiazol-2-yl)heptanoic acid methyl ester (407 mg, 1.2 mmol) in a mixture of water (7 ml) and dioxane (7 ml) was added dropwise aqueous 2N sodium hydroxide (4 ml) at room temperature and the mixture was stirred for 5 hours at room temperature. To the mixture further aqueous 2N sodium hydroxide (2 ml) was added dropwise and the resulting mixture was stirred for 1 hour, then diluted with water and extracted with ethyl acetate. The aqueous phase was acidified with hydrochloric acid and extracted with ethyl acetate. The organic layer was washed with water, dried and then evaporated to yield a residue, which was crystallized from isopropyl ether to give 7-(4,5,7-trifluorobenzothiazol-2-yl)heptanoic acid (189 mg, 50%) as a colorless powder.

m.p.116° to 118° C.

NMR(CDCl$_3$) δ:1.3–1.5 (4H,m), 1.8–1.5 (2H,m), 1.8–2.0 (2H,m), 2.37 (2H,t,J=7.4 Hz), 3.15 (2H,t,J=7.8 Hz), 6.9–7.1 (1H,m)

MS:317 (M$^+$), 258,216,203

Example 15 i) Sodium hydride (60% in oil, 220 mg, 5.5 mmol) was suspended in DMF (2 ml) and the suspension was stirred on a water bath. To the suspension was added dropwise a solution of 4,5,7-trifluoro-2-mercaptobenzothiazole (1.1 g, 5 mmol) in DMF (5 ml) under ice cooling and the mixture was stirred for 30 min. at room temperature and then cooled on a water bath. To the cooled mixture was added dropwise a solution of ethyl 5-bromopentanoate (1.05 g, 5 mmol) in DMF (3 ml) and the mixture was stirred for 2 hours at room temperature. The resultant mixture was diluted with water, then acidified with 7% hydrochloric acid and extracted with ethyl acetate. The organic layer was washed with an aqueous saturated saline solution, dried and then evaporated. The resulting residue was purified on a silica gel column to give 5-(4,5,7-trifluorobenzothiazol-2-ylthio)pentanoic acid ethyl ester (1.1 g, 64%) as an oil.

NMR(CDCl$_3$) δ:1.26 (3H,t,J=7 Hz), 1.75–1.95 (4H,m), 2.38 (2H,t, J=6.9 Hz), 3.42 (2H,t,J=6.9 Hz), 4.15 (2H,q,J= 7.1 Hz), 6.89–6.98 (1H,m)

MS:349 (M$^+$), 303,247,221 ii) To a mixture of dioxane (5 ml), methanol (2.5 ml) and water (2.5 ml) was added 5-(4,5,7-trifluorobenzothiazol-2-ylthio)pentanoic acid ethyl ester (590 mg, 2 mmol) and sodium hydroxide (100 mg, 2.5 mmol) and the resultant mixture was stirred for 15 hours at room temperature. The reaction mixture was diluted with water and washed with ether. The aqueous phase was then acidified with 7% hydrochloric acid and extracted with ethyl acetate. The organic phase was washed with an aqueous saturated saline solution, dried and then evaporated. The resulting oily residue was purified on a silica gel column and crystallized from hexane-isopropyl ether to give 5-(4,5,7-trifluorobenzothiazol-2-ylthio)pentanoic acid (170 mg, 31%) as a colorless powder.

m.p.56° to 58° C.

NMR(CDCl$_3$) δ:1.78–1.99 (4H,m), 2.45 (2H,t,J=7.1 Hz), 3.43 (2H,t, J=6.9 Hz), 6.88–6.99 (1H,m)

MS:321 (M$^+$), 248,234,221

Example 16 i) To a solution of 1,3-phenylene diacetic acid monoethyl ester (1.48 g, 6.7 mmol) in benzene (15 ml) was added dropwise thionyl chloride (1.6 g, 13.4 mmol) at room temperature and the mixture was heated to reflux for 2 hours. The solvent was then distilled off in vacuo leaving an acid chloride. The acid chloride was dissolved in NMP (2.0 ml) and stirred under a nitrogen stream during ice cooling. To the acid chloride solution was added dropwise a solution of 2-amino-4,6-difluorothiophenol (1.00 g, 6.2 mmol) in NMP (2.0 ml) and the resultant mixture was stirred overnight. After ice cooling, triethylamine (0.63 g, 6.2 mmol) was added to the ice cooled reaction mixture, which was then stirred at 100° C. for 6 hours. The reaction mixture was diluted with water and extracted with ethyl acetate. The organic layer was washed with aqueous sodium bicarbonate and a saturated saline solution successively, dried and then evaporated in vacuo to yield a oil residue. The resulting oily residue was purified on a silica gel column and crystallized from isopropyl ether to give ethyl 3-[(5,7-difluorobenzothiazol-2-yl)methyl]phenylacetate (0.690 g, 32%).

m.p.66° to 67° C.

NMR(CDCl$_3$) δ:1.24 (3H,t,J=7.3 Hz), 3.62 (2H,s), 4.15 (2H,q, J=7.3 Hz), 4.42 (2H,s), 7.2–7.4 (4H,m), 6.89 (1H, ddd,J=2.3,9.2 and 9.2 Hz), 7.51 (1H,bdd,J=2.3 and 9.2 Hz ).

MS:347 (M$^+$), 318,274.

ii) Ethyl 3-[(5,7-difluorobenzothiazol-2-yl)methyl]phenylacetate (610 mg, 1.8 mmol) was treated according to the procedure for Example 4-ii) and the resultant product was crystallized from isopropyl ether to give 3-[(5,7-difluorobenzothiazol-2-yl)methyl]phenylacetic acid (430 mg, 75%) as a white powder.

m.p.102° to 104° C.

NMR(CDCl$_3$) δ:3.66 (2H,s), 4.42 (2H,s), 6.88 (1H,ddd, J=2.3, 9.2 and 9.2 Hz), 7.2–7.4 (4H,m), 7.51 (1H,bdd, J=2.3 and 8.9 Hz).

MS:319 (M$^+$), 275,259.

Example 17 i) The procedure of Example 16-i) was repeated using 1,3-phenylene diacetic acid monoethyl ester (2.87 g, 10.5 mmol) and 2-amino-5,6-difluorothiophenol (2.0 g, 11.7 mmol) to obtain ethyl 3-[(6,7-difluorobenzothiazol-2-yl)methyl]phenylacetate (1.89 g, 44%) as a pale yellow oil.

NMR(CDCl$_3$) δ:1.24 (3H,t,J=7.3 Hz), 3.62 (2H,s), 4.15 (2H,q, J=7.3 Hz), 4.40 (2H,s), 7.2–7.4 (4H,m), 7.6–7.8 (1H,m).

MS:347 (M$^+$), 318,301,274.

ii) Ethyl 3-[(6,7-difluorobenzothiazol-2-yl)methyl]phenylacetate (1.2 g, 3.5 mmol) was treated according to the procedure for Example 4-ii) and the resultant product was crystallized from isopropyl ether to give 3-[(6,7-difluorobenzothiazol-2-yl)methyl]phenylacetic acid (1.0 g, 90%) as a colorless powder.

m.p.109° to 111° C.

NMR(CDCl$_3$) δ:3.66 (2H,s), 4.41 (2H,s), 7.2–7.4 (5H,m), 7.6–7.8 (1H,m).

MS:319 (M$^+$), 275,136.

Example 18 i) The procedure of Example 16-i) was repeated using 1,4-phenylene diacetic acid monoethyl ester (510 mg, 2.1 mmol) and 2-amino-3,4,6-trifluorothiophenol hydrochloride (2.0 g, 11.7 mmol) to obtain ethyl 4-[(4,5,7-trifluorobenzothiazol-2-yl)methyl]phenylacetate (270 mg, 35%) as a colorless powder.

m.p.75° to 77° C.

NMR(CDCl$_3$) δ:1.26 (3H,t,J=7.1), 3.62 (2H,s), 4.16 (2H, q, J=7.1 Hz), 4.44 (2H,s), 6.9–7.1 (1H,m), 7.29 (2H, br.d, J=8.6 Hz), 7.34 (2H,br.d,J=8.6 Hz).

MS:365 (M$^+$), 292,146,104.

ii) Ethyl 4-[(4,5,7-trifluorobenzothiazol-2-yl)methyl]phenylacetate (250 mg, 0.7 mmol) was treated according to the procedure for Example 4-ii) and the resultant product was crystallized from ethyl acetate to give 4-[(4,5,7-trifluorobenzothiazol-2-yl)methyl]phenylacetic acid (98 mg, 42%) as colorless plate crystals.

m.p.173° to 175° C.

NMR(CDCl$_3$) δ:3.67 (2H,s), 4.45 (2H,s), 6.9–7.1 (1H,m), 7.30 (2H,br.d,J=8.6 Hz), 7.35 (2H,br.d,J=8.6 Hz).

MS:337 (M$^+$), 292,267.

Example 19 i) The procedure of Example 16-i) was repeated using 1,3-phenylene diacetic acid monoethyl ester (847 mg, 3.3 mmol) and 2-amino-3,4-dichlorothiophenol hydrochloride (831 mg, 4.3 mmol) to obtain ethyl 3-[(4,5-dichlorobenzothiazol-2-yl)methyl]phenylacetate (706 mg, 56%) as a pale yellow oil.

NMR(CDCl$_3$) δ:1.24 (3H,t,J=7.3 Hz), 4.48 (2H,s), 3.61 (2H,s), 4.15 (2H,q,J=7.3), 7.2–7.4 (4H,m), 7.41 (1H,d, J=8.6 Hz), 7.58 (1H,d,J=8.6 Hz).

MS:379 (M$^+$), 306,291.

ii) Ethyl 3-[(4,5-dichlorobenzothiazol-2-yl)methyl]phenylacetate (647 mg, 1.7 mmol) was treated according to the procedure for Example 4-ii) and the resultant product was crystallized from methanol to give 3-[(4,5-dichlorobenzothiazol-2-yl)methyl]phenylacetic acid (477 mg, 80%) as needles.

m.p.150° to 152° C.

NMR(CDCl$_3$) δ:3.66 (2H,s), 4.48 (2H,s), 7.2–7.4 (4H,m), 7.57 (1H,d,J=8.6 Hz), 7.58 (1H,d,J=8.6 Hz).

MS:351 (M$^+$), 307,291,152.

Example 20 i) To a solution of 1,2-phenylene diacetic acid (2.0 g, 10.3 mmol) in benzene (40 ml) was added gradually thionyl chloride (6.20 g, 51.8 mmol) at room temperature and the mixture was heated to reflux for 2 hours. After cooling, the solvent was then distilled off in vacuo leaving an acid chloride. The acid chloride (2.38 g, 10.3 mmol) was dissolved in NMP (10 ml) and stirred under ice cooling. To the acid chloride solution was added a solution of 2-amino-3, 4,6-trifluorothiophenol (0.615 g, 3.4 mmol) in NMP (10 ml) and the resultant mixture was stirred for 1 hour under a nitrogen stream followed by addition of ethanol (10 ml). An excess of ethanol was distilled off in vacuo. The mixture was stirred at 100° C. for 2 hours, then diluted with water and extracted with ethyl acetate. The organic layer was dried and concentrated in vacuo to yield a residue. The residue was purified on a silica gel column to give ethyl 2-[(4,5,7-trifluorobenzothiazol-2-yl)methyl]phenylacetate (0.503 g, 41%) as a pale yellow oil.

NMR(CDCl$_3$) δ:1.20 (3H,t,J=7.3 Hz), 3.71 (2H,s), 4.08 (2H,q, J=7.3 Hz), 4.56 (2H,s), 6.9–7.1 (1H,m), 7.3–7.4 (4H,m).

MS:365 (M$^+$), 319,290.

ii) Ethyl 2-[(4,5,7-trifluorobenzothiazol-2-yl)methyl]phenylacetate (445 mg, 1.2 mmol) was treated according to the procedure for Example 4-ii) and the resultant product was crystallized from chloroform-hexane to give 2-[(4,5,7-trifluorobenzothiazol-2-yl)methyl]phenylacetic acid (209 mg, 48%) as colorless needles.

m.p.124° to 126° C.

NMR(CDCl$_3$) δ:3.75 (2H,s), 4.52 (2H,s), 6.9–7.0 (1H,m), 7.2–7.4 (4H,m).

MS:337 (M$^+$), 319,290.

Example 21

To a solution of 1,3-phenylene diacetic acid (1.5 g, 7.7 mmol) in benzene (30 ml) was added gradually thionyl chloride (3.28 g, 27.6 mmol) at room temperature and the mixture was heated to reflux for 2 hours. The solvent was then distilled off in vacuo leaving an acid chloride. The acid chloride (1.05 g, 4.6 mmol) was dissolved in NMP (1.5 ml) and stirred under ice cooling. To the acid chloride solution was added dropwise 2-amino-3,4-difluorothiophenol (1.11 g, 6.9 mmol) and triethylamine (0.70 g, 6.9 mmol) and the resultant mixture was stirred at 100° C. for 2 hours under a nitrogen stream. The reaction mixture was diluted with water and extracted with ethyl acetate. The organic layer was dried and concentrated in vacuo to yield a residue. The residue was purified on a silica gel column and crystallized from isopropyl ether to give 3-[(4,5-difluorobenzothiazol-2-yl)methyl]phenylacetic acid (0.245 g, 17%) as a colorless powder.

m.p.154° to 155° C.

NMR(CDCl$_3$) δ:3.66 (2H,s), 4.45 (2H,s), 7.1–7.4 (5H,m), 7.4–7.5 (1H,m).

MS:319 (M$^+$), 275,156.

Example 22 i) A solution of 1,3-biscyanomethyl-5-methylbenzene (2.89 g, 17 mmol) and 2-amino-3,4,6-trifluorothiophenol hydrochloride (3.66 g, 17 mmol) in absolute ethanol was heated at 170° C. for 15 hours under a nitrogen stream in an autoclave. After the reaction, evaporation of the solvent left a residue, which was purified on a silica gel column and recrystallized from ethyl acetate-hexane to obtain 3-[(4,5,7-trifluorobenzothiazol-2-yl)methyl]-5-methylphenylacetonitrile (1.86 g, 33%).

m.p.110° to 113° C.

NMR(CDCl$_3$) δ:2.36 (3H,s), 3.71 (2H,s), 4.42 (2H,s), 6.95–7.05 (1H,m), 7.10–7.14 (3H,m).

MS:332 (M$^+$), 305,290.

ii) A solution of 3-[(4,5,7-trifluorobenzothiazol-2-yl)methyl]-5-methylphenylacetonitrile (420 mg, 1.27 mmol) in 50% sulfuric acid was heated to reflux for 2 hours, then diluted with water and extracted with ethyl acetate. The organic layer was washed with water, dried and evaporated to yield crude crystals, which was recrystallized from ethanol-hexane to obtain 3-[(4,5,7-trifluorobenzothiazol-2-yl)methyl]-5-methylphenylacetic acid (290 mg, 87%) as a colorless powder.

m.p.127° to 129° C.

NMR(CDCl$_3$) δ:2.34 (3H,s), 3.62 (2H,s), 4.41 (2H,s), 7.0–7.1 (4H,m).

MS:351 (M$^+$), 307.

Example 23 i) The procedure of Example 22-i) was repeated using 1,3-biscyanomethyl-5-methylbenzene (680 mg, 4 mmol) and 2-amino-3,4-difluorothiophenol hydrochloride (888 mg, 4.5 mmol) and the resultant product was recrystallized from ethyl acetate-hexane to give 3-[(4,5-difluorobenzothiazol-2-yl)methyl]-5-methylphenylacetonitrile (210 mg, 17%) as a colorless powder.

m.p.84° to 86° C.

NMR(CDCl$_3$) δ:2.36 (3H,s), 3.72 (2H,s), 4.42 (2H,s), 7.09–7.28 (4H,m), 7.45–7.50 (1H,m).

MS:314 (M$^+$), 287.

ii) 3-[(4,5-Difluorobenzothiazol-2-yl)methyl]-5-methylphenylacetonitrile (400 mg, 1.27 mmol) was treated according to the procedure for Example 22-ii) and the resultant product was recrystallized from ethanol-hexane to give 3-[(4,5-difluorobenzothiazol-2-yl)methyl]-5-methylphenylacetic acid (340 mg, 80%) as a colorless powder.

m.p.139° to 141° C.

NMR(CDCl$_3$) δ:2.33 (3H,s), 3.62 (2H,s), 4.40 (2H,s), 7.0–7.5 (5H,m).

MS:333 (M$^+$), 288,272.

Example 24 i) The procedure of Example 22-i) was repeated using 1,3-biscyanomethyl-2-chlorobenzene (870 mg, 4.4 mmol) and 2-amino-3,4-difluorothiophenol hydrochloride (956 mg, 4.8 mmol) and the resultant product was recrystallized from ethyl acetate-hexane to give 3-[(4,5-difluorobenzothiazol-2-yl)methyl]-2-chlorophenylacetonitrile (295 mg, 20%) as a colorless powder.

m.p.152° to 154° C.

NMR(CDCl$_3$) δ:3.89 (2H,s), 4.64 (2H,s), 7.22–7.55 (5H, m).

MS:334 (M$^+$), 299,259.

ii) 3-[(4,5-Difluorobenzothiazol-2-yl)methyl]-2-chlorophenylacetonitrile (400 mg, 1.20 mmol) was treated according to the procedure for Example 22-ii) and the resultant product was recrystallized from acetonitrile-ethanol to give 3-[(4,5-difluorobenzothiazol-2-yl)methyl]-2-chlorophenylacetic acid (380 mg, 90%) as a colorless powder.

m.p.198° C. (dec.)

NMR(CDCl$_3$) δ:3.66 (2H,s), 4.51 (2H,s), 7.15–7.48 (5H, m).

MS:318 (M$^+$–Cl), 272.

Example 25 i) The procedure of Example 22-i) was repeated using 1,3-biscyanomethyl-2-chlorobenzene (953 mg, 5 mmol) and 2-amino-3,4,6-trifluorothiophenol hydrochloride (1,078 mg, 10 mmol) and the resultant product was crystallized from ethyl acetate-hexane to give 3-[(4,5,7-trifluorobenzothiazol-2-yl)methyl]-2-chlorophenylacetonitrile (410 mg, 23%) as a colorless powder.

m.p.148° to 151° C.

NMR(CDCl$_3$) δ:3.89 (2H,s), 4.64 (2H,s), 7.0–7.1 (1H,m), 7.3–7.6 (3H,m).

MS:352 (M$^+$), 317,277.

ii) 3-[(4,5,7-Trifluorobenzothiazol-2-yl)methyl]-2-chlorophenylacetonitrile (370 mg, 1.05 mmol) was treated according to the procedure for Example 22-ii) and the resultant product was crystallized from ethanol-hexane to give 3-[(4,5,7-trifluorobenzothiazol-2-yl)methyl]-2-chlorophenylacetic acid 290 mg, 87%).

m.p.156° to 158° C.

NMR(CDCl$_3$) δ:3.89 (2H,s), 4.64 (2H,s), 6.96–7.05 (1H, m), 7.3–7.4 (3H,m).

MS:336 (M$^+$–Cl), 290.

Example 26 i) The procedure of Example 22-i) was repeated using 1,3-biscyanomethyl-5-fluorobenzene (1.6 g, 9.2 mmol) and 2-amino-3,4,6-trifluorothiophenol hydrochloride (1.98 g, 9.2 mmol) and the resultant product was crystallized from isopropyl ether to give 3-[(4,5,7-trifluorobenzothiazol-2-yl)methyl]-5-fluorophenylacetonitrile (868 mg, 28%) as a colorless powder.

m.p.91° to 94° C.

NMR(CDCl$_3$) δ:3.77 (2H,s), 4.46 (2H,s), 6.9–7.1 (3H,m), 7.14 (1H,bs).

MS:336 (M$^+$), 309,295.

ii) 3-[(4,5,7-Trifluorobenzothiazol-2-yl)methyl]-5-fluorophenylacetonitrile (600 mg, 2.4 mmol) was treated according to the procedure for Example 22-ii) and the resultant product was recrystallized from isopropyl ether to give 3-[(4,5,7-trifluorobenzothiazol-2-yl)methyl]-5-fluorophenylacetic acid (717 mg, 85%) as a colorless powder.

m.p.139° to 142° C.

NMR(CDCl$_3$) δ:3.66 (2H,s), 4.44 (2H,s), 6.9–7.1 (3H,m), 7.08 (1H,bs).

MS:355 (M$^+$), 311,295.

Example 27 i) The procedure of Example 22-i) was repeated using 1,3-biscyanomethyl-5-chlorobenzene (650 mg, 3.4 mmol) and 2-amino-3,4,6-trifluorothiophenol hydrochloride (735 mg, 3.4 mmol) and the resultant product was crystallized from isopropyl ether to give 3-[(4,5,7-trifluorobenzothiazol-2yl)methyl]-5-chlorophenylacetonitrile (333 mg, 28%) as a colorless powder.

m.p.114° to 117° C.

NMR(CDCl$_3$) δ:3.75 (2H,s), 4.45 (2H,s), 6.9–7.1 (1H,s), 7.24 (1H,bs), 7.31 (1H,bs), 7.35 (1H,bs).

MS:352 (M$^+$), 325,277.

ii) 3-[(4,5,7-Trifluorobenzothiazol-2-yl)methyl]-5-chlorophenylacetonitrile (300 mg, 0.8 mmol) was treated according to the procedure for Example 22-ii) and the resultant product was recrystallized from isopropyl ether to give 3-[(4,5,7-trifluorobenzothiazol-2-yl)methyl]-5-chlorophenylacetic acid (244 mg, 77%) as a colorless powder.

m.p.177° to 179° C.

NMR(CDCl$_3$) δ:3.64 (2H,s), 4.43 (2H,s), 6.9–7.1 (1H,m), 7.19 (1H,bs), 7.26 (1H,bs), 7.29 (1H,bs).

MS:371 (M$^+$), 327,290.

Example 28 i) The procedure of Example 22-i) was repeated using 1,3-biscyanomethyl-5-bromobenzene (1.9 g, 8.1 mmol) and 2-amino-3,4,6-trifluorothiophenol hydrochloride (1.74 g, 8.1 mmol) and the resultant product was crystallized from isopropyl ether to give 3-[(4,5,7-trifluorobenzothiazol-2-yl)methyl]-5-bromophenylacetonitrile (532 mg, 18%) as a colorless powder.

m.p.119° to 124° C.

NMR(CDCl$_3$) δ:3.74 (2H,s), 4.44 (2H,s), 6.9–7.1 (1H,m), 7.29 (1H,bs), 7.47 (1H,bs), 7.50 (1H,bs).

MS:396 (M$^+$), 371,277.

ii) 3-[(4,5,7-Trifluorobenzothiazol-2-yl)methyl]-5-bromophenylacetonitrile (500 mg, 1.2 mmol) was treated according to the procedure for Example 22-ii) and the resultant product was recrystallized from isopropyl ether to give 3-[(4,5,7-trifluorobenzothiazol-2-yl)methyl]-5-bromophenylacetic acid (372 mg, 71%) as a colorless powder.

m.p.183° to 185° C.

NMR(CDCl$_3$) δ:3.64 (2H,s), 4.42 (2H,s), 6.9–7.1 (1H,m), 7.24 (1H,bs), 7.42 (1H,bs), 7.45 (1H,bs).

MS:415 (M$^+$), 371,290.

Example 29 i) The procedure of Example 22-i) was repeated using 1,3-biscyanomethyl-5-iodobenzene (420 mg, 1.49 mmol) and 2-amino-3,4,6-trifluorothiophenol hydrochloride (321 mg, 1.49 mmol) and the resultant product was crystallized from ethyl acetate-hexane to give 3-[(4,5,7-trifluorobenzothiazol-2-yl)methyl]-5-iodophenylacetonitrile (240 mg, 36%) as a colorless powder.

m.p.127° to 130° C.

NMR(CDCl$_3$) δ:3.72 (2H,s), 4.41 (2H,s), 7.0–7.1 (1H,m), 7.32 (1H,bs), 7.66 (1H,bs), 7.70 (1H,bs).

MS:444 (M$^+$), 417,277.

ii) 3-[(4,5,7-Trifluorobenzothiazol-2-yl)methyl]-5-iodophenylacetonitrile (240 mg, 0.54 mmol) was treated according to the procedure for Example 22-ii) and the resultant product was recrystallized from ethyl acetate-hexane to give 3-[(4,5,7-trifluorobenzothiazol-2-yl)methyl]-5-iodophenylacetic acid (163 mg, 65%) as a colorless powder.

m.p.171° to 173° C.

NMR(CDCl$_3$) δ:3.61 (2H,s), 4.40 (2H,s), 7.0–7.1 (1H,m), 7.27 (1H,bs), 7.62 (1H,bs), 7.65 (1H,bs).

MS:463 (M$^+$), 419,290.

Example 30 i) The procedure of Example 22-i) was repeated using 3,5-biscyanomethylbenzoic acid (1,819 mg, 8.5 mmol) and 2-amino-3,4,6-trifluorothiophenol hydrochloride (2,015 mg, 9.3 mmol) and the resultant product was crystallized from ethyl acetate-hexane to give methyl 3-[(4,5,7-trifluorobenzothiazol-2-yl)methyl]-5-cyanomethylbenzoate (470 mg, 15%) as a colorless powder.

m.p.130° to 132° C.

NMR(CDCl₃) δ:3.82 (2H,s), 3.94 (3H,s), 4.53 (2H,s), 7.56 (1H,s), 7.98 (1H,s), 8.03 (1H,s).

MS:376 (M⁺), 349,316,277.

ii) Methyl 3-[(4,5,7-trifluorobenzothiazol-2-yl)methyl]-5-cyanomethylbenzoate (376 mg, 1 mmol) was treated according to the procedure for Example 22-ii) and the resultant product was recrystallized from ethyl acetate-isopropyl ether to give 3-[(4,5,7-trifluorobenzothiazol-2-yl)methyl]-5-carboxymethylbenzoic acid (170 mg, 45%) as a colorless powder.

m.p.203° to 205° C.

NMR(CDCl₃) δ:3.65 (2H,s), 4.51 (2H,s), 7.0–7.1 (1H,m), 7.51 (1H,s), 7.95 (2H,s).

MS:381 (M⁺), 335,319,290.

Example 31 i) The procedure of Example 22-i) was repeated using 1,3-biscyanomethyl-5-dimethylaminobenzene (440 mg, 2.2 mmol) and 2-amino-3,4,6-trifluorothiophenol hydrochloride (474 mg, 2.2 mmol) and the resultant product was crystallized from isopropyl ether to give 3-[(4,5,7-trifluorobenzothiazol-2-yl)methyl]-5-dimethylaminophenylacetonitrile (234 mg, 30%) as a colorless powder.

m.p.99° to 100° C.

NMR(CDCl₃) δ:2.98 (6H,s), 3.70 (2H,s), 4.39 (2H,s), 6.58 (1H,s), 6.62 (2H,s), 6.9–7.0 (1H,m).

MS:361 (M⁺).

ii) 3-[(4,5,7-Trifluorobenzothiazol-2-yl)methyl]-5-dimethylaminophenylacetonitrile (200 mg, 0.55 mmol) was treated according to the procedure for Example 22-ii) and the resultant product was recrystallized from ethanol-hexane to give 3-[(4,5,7-trifluorobenzothiazol-2-yl)methyl]-5-dimethylaminophenylacetic acid (158 mg, 75%) as a colorless powder.

m.p.114° to 115° C.

NMR(CDCl₃) δ:2.96 (6H,s), 3.61 (2H,s), 4.39 (2H,s), 6.58 (1H,s), 6.61 (1H,s), 6.64 (1H,s), 6.9–7.0 (1H,m).

MS:380 (M⁺), 336,319,290.

Example 32 i) N-[3-(4,5,7-Trifluorobenzothiazol-2-yl)propionyl]-N-phenylglycine methyl ester (365 mg, 0.9 mmol) was treated according to the procedure for Example 7-i) and the resultant product was purified on a silica gel column to obtain N-[3-(4,5,7-trifluorobenzothiazol-2-yl)-1-thioxopropionyl]-N-phenylglycine methyl ester (310 mg, 73%) as an oil.

NMR(CDCl₃) δ:3.02 (2H,t,J=6.9 Hz), 3.69 (2H,t,J=6.9 Hz), 3.75 (3H,s), 4.90 (2H,s), 6.9–7.0 (1H,m), 7.3–7.5 (5H,m).

MS:424 (M⁺), 316,216.

ii) N-[3-(4,5,7-Trifluorobenzothiazol-2-yl)-1-thioxopropionyl]-N-phenylglycine methyl ester (300 mg, 0.7 mmol) was treated according to the procedure for Example 4-ii) and the resultant product was crystallized from isopropyl ether to obtain N-[3-(4,5,7-trifluorobenzothiazol-2-yl)-1-thioxopropionyl]-N-phenylglycine (235 mg, 82%) as a pale brown powder.

m.p.173° to 176° C.

NMR(CDCl₃) δ:3.02 (2H,t,J=6.9 Hz), 3.69 (2H,t,J=6.9 Hz), 4.94 (2H,s), 6.9–7.0 (1H,m), 7.3–7.5 (5H,m).

MS:410 (M⁺), 245,217.

Formulation Example 1

| Tablet | |
|---|---|
| (Total amount per tablet: 200 mg) | |
| a) Compound of the invention | 50 mg |
| b) Crystalline Cellulose | 100 mg |
| c) Lactose | 48 mg |
| d) Maize Starch | 50 mg |
| e) Magnesium Stearate | 2 mg |

The ingredients (a), (b), (c), (d) and (e) were formulated into tablets by known methods according to general pharmaceutical rules prescribed in Japanese Pharmacopoeia (JPXII).

Formulation Example 2

| Capsule | |
|---|---|
| (Total amount per capsule: 200 mg) | |
| a) Compound of the invention | 50 mg |
| b) Lactose | 120 mg |
| c) Maize Starch | 28 mg |
| d) Magnesium Stearate | 2 mg |

The ingredients (a), (b), (c) and (d) were formulated into capsules by known methods according to general pharmaceutical rules prescribed in JPXII.

Example 3

| Injection | |
|---|---|
| (Total amount per ampoule: 2 ml) | |
| a) Compound of the invention | 5 mg |
| b) Sodium Chloride | 3 mg |
| c) Conventional pH Regulator (adjusted to pH 6.5 to 7.5) | suitable amount |
| d) Methylparaben | 1 mg |
| e) Water for Injection | suitable amount |

The ingredients (a), (b), (c), (d) and (e) were formulated into injectable solutions by known methods according to general pharmaceutical rules prescribed in JPXII.

Example 4

| Eyedrop | |
|---|---|
| (Total amount per container: 15 ml) | |
| a) Compound of the invention | 10 mg |
| b) Sodium Chloride | 10 mg |
| c) Methylparaben | 7.5 mg |
| d) Sterile Distilled Water | suitable amount |

The ingredients (a), (b), (c) and (d) were formulated into eyedrops by known methods according to general pharmaceutical rules prescribed in JPXII.

The compounds of the present invention exert potent aldose reductase inhibiting actions and useful in the prophylactic or therapeutic treatment of diabetic complications such as cataract, keratopathy, retinopathy, peripheral and autonomic neuropathy, nephropathy and the like. The compound may be applied orally or parenterally for prophylactic or therapeutic purposes.

What is claimed is:

1. A benzothiazole derivative compound of the formula (1):

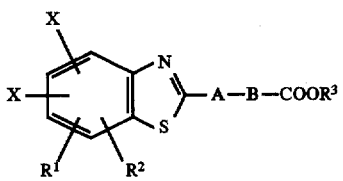

wherein:

X is halogen, $R^1$ and $R^2$ which are the same or different are each independently hydrogen of halogen, A is a methylene group, and —B—$COOR^3$ is a group represented by the following formula (2):

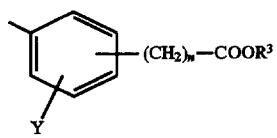

wherein $R^3$ is hydrogen or a C1 to C3 lower alkyl, Y is hydrogen, halogen, C1 to C3 lower alkyl, carboxyl or dilower alkylamino and n is an integer of 1 to 3; or —B—$COOR^3$ is a group represented by the following formula (3):

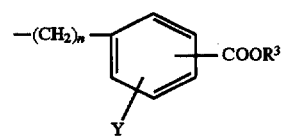

wherein R3 is hydrogen or a C1 to C3 lower alkyl, Y is hydrogen, halogen, C1 to C3 lower alkyl, carboxyl or dilower alkylamino and n is an integer of 1 to 3;

or a pharmaceutically acceptable salt thereof.

2. The benzothiazole derivative compound according to claim 1, wherein —B—$COOR^3$ is a group represented by the following formula (2):

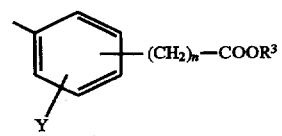

wherein $R^3$ is hydrogen or C1 to C3 lower alkyl, Y is hydrogen, halogen, C1 to C3 lower alkyl, carboxyl or dilower alkylamino and n is an integer of 1 to 3, or a pharmaceutically acceptable salt thereof.

3. The benzothiazole derivative compound according to claim 2, which is a compound represented by the following formula (6):

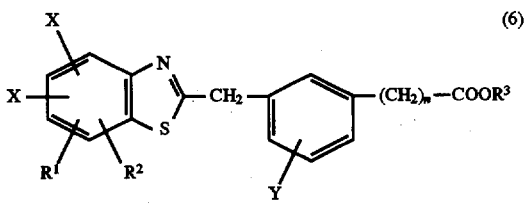

wherein X is halogen, $R^1$ and $R^2$, which are the same or different, are each independently hydrogen or halogen, $R^3$ is hydrogen or C1 to C3 lower alkyl, Y is hydrogen, halogen, C1 to C3 lower alkyl, carboxyl or dilower alkylamino and n is an integer of 1 to 3, or a pharmaceutically acceptable salt thereof.

4. The benzothiazole derivative compound according to claim 3, wherein X is fluorine, or a pharmaceutically acceptable salt thereof.

5. The benzothiazole derivative compound according to claim 4, wherein n is 1, or a pharmaceutically acceptable salt thereof.

6. The benzothiazole derivative compound according to claim 1, wherein —B—$COOR^3$ is a group represented by the following formula (3):

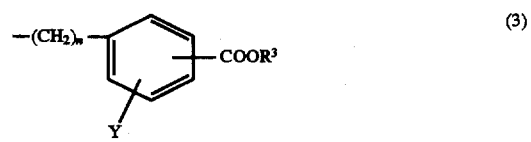

wherein $R^3$ is hydrogen or C1 to C3 lower alkyl, Y is hydrogen, halogen, C1 to C3 lower alkyl, carboxyl or dilower alkylamino and n is an integer of 1 to 3, or a pharmaceutically acceptable salt thereof.

7. The benzothiazole derivative compound according to claim 6, which is a compound represented by the following formula (7):

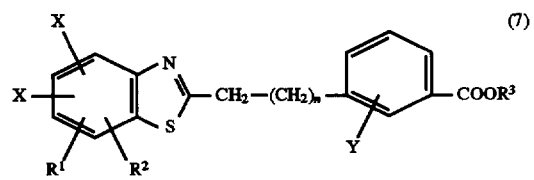

wherein X is halogen, $R^1$ and $R^2$, which are the same or different, are each independently hydrogen or halogen, $R^3$ is hydrogen or C1 to C3 lower alkyl, Y is hydrogen, halogen, C1 to C3 lower alkyl, carboxyl or dilower alkylamino and n is an integer of 1 to 3, or a pharmaceutically acceptable salt thereof.

8. The benzothiazole derivative compound according to claim 7, wherein X is fluorine, or a pharmaceutically acceptable salt thereof.

9. The benzothiazole derivative compound according to claim 8, wherein n is 1, or a pharmaceutically acceptable salt thereof.

10. A pharmaceutical composition which comprises an effective amount of a compound according to claim 1 or a pharmaceutically acceptable salt thereof in admixture with a pharmaceutically acceptable carrier.

11. The pharmaceutical composition according to claim 10, which is an aldose reductase inhibitor.

12. The pharmaceutical composition according to claim 10, which is a prophylactic or therapeutic agent for the treatment of diabetic complications.

13. A method for treating diabetic complications, which comprises administering an effective amount of a pharmaceutical composition according to claim 10 to a patient in need thereof.

14. A method for inhibiting aldose reductase in a patient which comprises administering an effective amount of a pharmaceutical composition according to claim 10 to a patient in need thereof.

* * * * *